United States Patent
Guy et al.

(10) Patent No.: US 8,278,428 B2
(45) Date of Patent: Oct. 2, 2012

(54) MITOCHONDRIAL NUCLEIC ACID DELIVERY SYSTEMS

(75) Inventors: John Guy, Gainesville, FL (US); Nicholas Muzyczka, Gainesville, FL (US)

(73) Assignee: John Guy, Miami Beach, FL (US)

( * ) Notice: Subject to any disclaimer, the term of this patent is extended or adjusted under 35 U.S.C. 154(b) by 324 days.

(21) Appl. No.: 12/526,878

(22) PCT Filed: Feb. 18, 2008

(86) PCT No.: PCT/US2008/054216
§ 371 (c)(1), (2), (4) Date: Jan. 5, 2010

(87) PCT Pub. No.: WO2008/101233
PCT Pub. Date: Aug. 21, 2008

(65) Prior Publication Data
US 2010/0111911 A1    May 6, 2010

Related U.S. Application Data

(60) Provisional application No. 60/890,403, filed on Feb. 16, 2007.

(51) Int. Cl.
*C07H 21/02* (2006.01)
*C07H 21/04* (2006.01)
*A61K 48/00* (2006.01)

(52) U.S. Cl. ............. 536/23.1; 536/23.5; 514/44 R
(58) Field of Classification Search ............ 536/23.1, 536/23.5; 514/44 R
See application file for complete search history.

(56) References Cited

U.S. PATENT DOCUMENTS

| | | | |
|---|---|---|---|
| 4,797,368 A | 1/1989 | Carter et al. | |
| 5,139,941 A | 8/1992 | Muzyczka et al. | |
| 5,399,346 A | 3/1995 | Anderson et al. | |
| 7,405,284 B2 * | 7/2008 | Guy | 536/23.1 |
| 7,691,809 B2 | 4/2010 | Kruzel et al. | |
| 2004/0072774 A1 | 4/2004 | Manfredi et al. | |
| 2004/0142419 A1 | 7/2004 | Guy | |
| 2005/0031593 A1 * | 2/2005 | Harding et al. | 424/93.2 |
| 2005/0250202 A1 * | 11/2005 | March et al. | 435/366 |
| 2006/0003338 A1 | 1/2006 | Deng et al. | |

FOREIGN PATENT DOCUMENTS

| | | |
|---|---|---|
| CA | 2 273 173 | 5/1999 |
| WO | WO 2005/001062 | 1/2005 |
| WO | WO 2005/056752 | 6/2005 |
| WO | WO 2007/008486 | 1/2007 |
| WO | PCT/US07/081922 | 10/2007 |

OTHER PUBLICATIONS

Hauswirth et al. Production and purification of recombinant adeno-associated virus. Methods Enzymol. 316:743-761, 2000.*

D'Souza, G.G.M. et al. (2007) "Gene Therapy of the Other Genone: The Challenges of Treating Mitochondrial DNA Defects", Pharmaceutical Research, 24 (2): 228-238.
Zuo, X. et al. (2007) "A functional core of the mitochondrial genome maintenance protein Mgm101p in *Saccharomyces cerevisiae* determined with a temperature-conditional allele", FEMS Yeast Res 7. 131-140.
Qi, X. et al. (2004) "SOD2 Gene Transfer Protects against Optic Neuropathy Induced by Deficiency of Complex I", Ann. Neurol. 56: 182-191.
Curiel, D.T. et al. (1991) Andenovirus enhancement of transferrin—polylysine-mediated gene delivery, Proc. Natl. Acad. Scie. USA (88), pp. 8850-8854.
Fleming, J. et al. (2005) Partial Correction of Sensitivity to Oxidant Stress in Friedreich Ataxia Patient Fibroblasts by Frataxin-Encoding Adeno-Associated Virus and Lentivirus Vectors, Hum. Gene Therapy. (16) pp. 947-956.
Mochizuki, H. et al. (2002) Adeno-associated virus-mediated antiapoptotic gene delivery: in vivo gene therapy for neurological disorders, Methods. (28) pp. 248-252.
Owen, R. et al. (2000) Recombinant Adeno-Associated Virus Vector-Based Gene Transfer for Defects in Oxidative Metabolism, Hum. Gene Therapy. (11) pp. 2067-2078.
Alexander, I.E. et al. (2008) Potential of AAV vectors in the treatment of metabolic disease, Gene Therapy 15: 831-839.
Del Gaizo, V. et al. (2003) Targeting proteins to mitochondria using TAT, Mol. Genet. Metab. 80: 170-180.
Furler, S. et al. (2001) Recombinant AAV vectors containing the foot and mouth disease virus 2A sequence confer efficient bicistronic gene expression in cultured cells and rat substantia nigra neurons, Gene Therapy 8: 864-873.
Guy, J. et al. (2002) Rescue of a Mitochondrial Deficiency Causing Leber Hereditary Optic Neuropathy, Ann Neurol 52: 534-542.
Guy, J. et al. (2009) Efficiency and Safety of AAV-Mediated Gene Delivery of the Human ND4 Comples I Subunit in the Mouse Visual System, Investigative Ophthalmology & Visual Science, 50(9): 4205-4214.
Kawamoto, S. et al. (2005) Widespread and Early Myocardial Gene Expression by Adeno-associated Virus Vector Type 6 with a β-Actin Hybrid Prometer, Mol. Ther. 11: 980-985.
Keeney, P.M. (2009) Mitochondrial Gene Therapy Augments Mitochondrial Physiology in a Parkinson's Disease Cell Model, Human Gene Therapy 20: 897-907.
Khan, S.M. et al. (2004) Development of Mitochondrial Gene Replacement Therapy, J. Bioenerg. Biomembr. 36 (4): 387-393.
Koilkonda, R.D. et al. (2009) Efficient expression of self-complimentary AAV in ganglion cells of the ex vivo primate retina, Molecular Vision 15: 2796-2802.
Qi, X. et al., "Mitochondrial Superoxide Dismutase Modulates Experimental Optic Neuritis", Investigative Ophthalmology & Visual Science, vol. 45: E-Abstract 1558 (2004).
Qi, et al. (2007) "The Mutant Human ND4 Subunit of Complex I Induces Optic Neuropathy in the Mouse," Investigative Ophthalmology & Visual Science. 48(1): 1-10.
Epperly et al., (Radiat Res, 160(5): pp. 568-578, 2003).

(Continued)

*Primary Examiner* — Wu-Cheng Winston Shen
(74) *Attorney, Agent, or Firm* — Novak Druce + Quigg

(57) ABSTRACT

Nucleic acid mitochondrial delivery systems are provided. These systems are important for delivery of genetic information to a mitochondrion and for treatment of mitochondrial related diseases.

18 Claims, 7 Drawing Sheets

OTHER PUBLICATIONS

Melov et al., (Nature Genetics, 18: pp. 159-163, 1998).

Sun, et al., "AAV-Mediated *Sod2* Gene Expression Driven by a Pro-Inflammatory Inducible Promoter: A Novel Method for Gene Therapy of Multiple Sclerosis", Investigative Ophthalmology & Visual Science, 44: E-Abstrct 628, XP009152147 (2003).

Qi, et al., "Mitochondria Play a Role in the Neurodegeneration of an Animal Model of Multiple Sclerosis", Neurology, vol. 66, suppl. 2, p. A14 (Mar. 2006).

Qi, et al., "Use of Mitochondrial Antioxidant Defenses for Rescue of Cells With a Leber Hereditary Optic Neuropathy-Causing Mutation", "Laboratory Sciences", ARCH Ophthalmology, vol. 125, No. 2, pp. 268-272 (2007).

Qi, et al., "Suppression of Mitochondrial Oxidative Stress Provides Long-term Neuroprotection in Experimental Optic Neuritis", Investigative Ophthalmology & Visual Science, Association for Research in Vision and Ophthalmology, vol. 48, No. 2, pp. 681-691(Feb. 2007).

Fleming, A. (Jun. 2012) Crossing mitochondrial barriers, Nature Reviews/Drug Discovery, Gene Therapy, vol. 11.

Yu et al. (Apr. 2012) Gene delivery to mitochondria by targeting modified adenoassociated virus suppresses Leber's hereditary optic neuropathy in a mouse model, PNAS.org, pp. E1238-E1247.

Barbel Kaufmann, et al., The Structure of Human Parvovirus B19, Proc Natl Acad Sci. 101, 11628-11633, 2004.

Edward B. Miller, et al., Production, Purification and Preliminary X-ray Crystallographic Studies of Adeno-associated Virus Serotype 1, Acta Cryst. F62, 1271-1274, 2006.

\* cited by examiner 915 bp

MITOCHONDRIAL NUCLEIC ACID DELIVERY SYSTEMS

CROSS-REFERENCE TO RELATED APPLICATIONS

This application is a §371 national stage entry of International Application No. PCT/US2008/054216, filed Feb. 18, 2008, which claims priority to U.S. Provisional Application No. 60/890,403, filed Feb. 16, 2007, both of which are hereby incorporated by reference.

FIELD OF THE INVENTION

The invention is related to mitochondrial delivery systems and expression of mitochondrial genes.

BACKGROUND

In only 16,600 base pairs, human mitochondrial DNA (mtDNA) encodes 37 genes (2 for ribosomal RNAs, 22 for tRNAs and 13 for proteins) that are essential for cell viability. These genes are buffered against the effect of mutations, because somatic cells typically contain around 1000 copies of mtDNA. While most cells are apparently uniform with respect to mtDNA composition, mammalian cells can tolerate a significant fraction of aberrant mtDNA, a condition called heteroplasmy, and retain respiratory function. Nevertheless, mitochondria lack nucleotide excision and recombination repair systems, so that, with age, deletions and point mutations accumulate in mtDNA. This accretion of defects is thought to contribute to the infirmities of advanced age.

Significant obstacles remain to correcting any mtDNA in living animals since there is no delivery system for DNA into mitochondria. Therefore, a need exists in the art for the targeting and delivery of nucleic acids and other therapeutic molecules into the mitochondria.

SUMMARY

Compositions for introducing nucleic acid molecules into mitochondria are provided. These compositions are used, inter alia, for correcting point mutations in mitochondrial protein-coding genes. Nucleic acid molecules such as cDNA coded in the mitochondrial genetic code are directly introduced into the mitochondria. Methods for introducing nucleic acid molecules are described.

In one preferred embodiment, a composition comprises a nucleic acid backbone or vector comprising a mitochondrial targeting sequence; a mitochondrial gene operably linked to a mitochondrial promoter. Any of these components can be in single copies; multiple copies; combinations of single copies of one component and multiple copies of another; and components can be tandem repeats or otherwise.

The recombinant vectors can be DNA plasmids or viral vectors. Mitochondrial gene expressing viral vectors can be constructed based on, but not limited to, adeno-associated virus, retrovirus, adenovirus, or alphavirus. The recombinant vectors capable of expressing the mitochondrial molecules can be delivered as described herein, and persist in the mitochondria. Alternatively, viral vectors can be used that provide for transient expression of mitochondrial molecules. Such vectors can be repeatedly administered as necessary. Once expressed, the mitochondrial molecules compensate for the gene function or expression of the mutated mitochondrial gene. Delivery of mitochondrial gene expressing vectors can be systemic, such as by intravenous or intramuscular administration, by administration to target cells ex-planted from a subject followed by reintroduction into the subject, or by any other means that would allow for introduction into the desired target cell.

In a preferred embodiment, a composition comprises a nucleic acid encoding a vector; mitochondrial promoters; a mitochondrial gene and a mitochondrial targeting sequence. The vector can be viral, non-viral, naked DNA and the like.

In one embodiment, the viral vector is an Adeno Associated virus (AAV) vector and the AAV vector comprises Rep, Cap, and inverted terminal repeat (ITR) sequences.

In one aspect, the mitochondrial targeting sequence is inserted into the AAV capsid open reading frame (cap ORF). However, the mitochondrial targeting sequences can be inserted into any region of a vector; insert single or multiple copies of the same or different targeting sequences.

In another preferred embodiment, the AAV is selected from the group consisting of AAV-1 to AAV-9 serotypes. The AAV genome can comprise Rep and Cap genes from other AAV serotypes and/or the AAV can be pseudotyped.

In another preferred embodiment, the mitochondrial gene is a normal mitochondrial gene and expression thereof compensates for a mutated mitochondrial gene. Preferably, the vector comprises at least one mitochondrial gene and mitochondrial targeting sequences. In other aspects, the vector comprises at least one mitochondrial gene and two or more mitochondrial targeting sequences and combinations thereof. Other examples, include a vector comprising multiple copies of the mitochondrial gene and/or mitochondrial targeting sequences. The vector can comprises one or more types of mitochondrial genes and/or mitochondrial targeting sequences; fragments and variants thereof.

In another preferred embodiment, the nucleic acids of the mitochondrial gene comprise mitochondrial codons from the mitochondrial genome.

In another preferred embodiment, an Adenovirus Associated Virion comprising a mitochondrial targeting sequence; a mitochondrial gene operably linked to a mitochondrial promoter. Preferably, the mitochondrial gene is operably linked to the mitochondrial promoter and inserted into the AAV vector backbone.

In another preferred embodiment, the AAV is selected from the group consisting of AAV-1 to AAV-9 serotypes. The AAV can also be pseudotyped, comprise Rep and Cap genes from other AAV serotypes; and/or mutated Cap genes.

In another preferred embodiment, the AAV comprises a normal mitochondrial gene and expression thereof compensates for a mutated mitochondrial gene and a mitochondrial targeting sequence; fragments and variants thereof.

In one preferred embodiment, the AAV comprises at least one mitochondrial gene and mitochondrial targeting sequences. The numbers and types of mitochondrial genes and sequences can vary. For example, in some embodiments, the AAV comprises at least one mitochondrial gene and two or more mitochondrial targeting sequences and combinations thereof. In other embodiments, the AAV n the vector comprises multiple copies of the mitochondrial gene and/or mitochondrial targeting sequences. In another embodiment, the AAV comprises one or more types of mitochondrial genes and/or mitochondrial targeting sequences.

In another preferred embodiment, a method of treating mitochondrial related diseases comprises administering to a patient a composition comprising an AAV vector encoding at least one mitochondrial gene wherein said gene is operably linked to a mitochondrial promoter, at least one mitochondrial targeting sequence; binding and entering of the AAV into mitochondria; expressing the mitochondrial gene in mitochondria wherein said gene is a normal gene and compensates for a mutation; and, treating mitochondrial related diseases.

In another preferred embodiment, the mitochondrial related diseases comprise: Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Stroke-like episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Opthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Opthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young, and MNGIE.

In another preferred embodiment, the mitochondrial targeting sequences comprise nucleic acid molecules encoding: cytochrome c oxidase (COX); ATP synthase; subunit c of human ATP synthase (ATPc); ATP synthase; hexokinase I, amine oxidase (flavin-containing) A, hexokinase IV, pancreatic beta cell form, peripheral benzodiazepine receptor-related protein, metaxin 2, putative mitochondrial outer membrane protein import receptor (hTOM), glutathione transferase; voltage-dependent anion channel 2 (outer mitochondrial membrane protein porin), hexokinase IV, cytochrome b5, peripheral benzodiazepine receptor, germ cell kinase anchor S-AKAP84, A kinase anchor protein, carnitine O-palmitoyltransferase I precursor, hexokinase II, amine oxidase (flavin-containing) B, long-chain-fatty-acid—CoA ligase 2, long-chain-fatty-acid—CoA ligase 1 (palmitoyl-CoA ligase), voltage-dependent anion channel 1, metaxin 1, Human putative outer mitochondrial membrane 34 kDa translocase hTOM34, voltage-dependent anion channel 4 (outer mitochondrial membrane protein porn), cytochrome-b5 reductase, voltage-dependent anion channel 3 (outer mitochondrial membrane protein porn), Mitochondrial import receptor subunit TOM20 homolog (Mitochondrial 20 kd outer membrane protein) (Outer mitochondrial membrane receptor TOM20), and tumorous imaginal discs homolog precursor (HTID-1); fragments and variants thereof.

In another preferred embodiment, a method for compensating for a mtDNA mutation in a host comprising: introducing a host's mitochondria a composition of AAV encoding mitochondrial promoters; a mitochondrial gene and a mitochondrial targeting sequence; fragments and variants thereof. Preferably the viral vector is an Adeno Associated virus (AAV) vector and the AAV vector comprises Rep, Cap, and inverted terminal repeat (ITR) sequences.

In a preferred embodiment, a method of introducing nucleic acid molecules into mitochondria (intra-mitochondrially) comprises administering to a patient a composition comprising a vector encoding at least one mitochondrial gene wherein said gene is operably linked to a mitochondrial promoter, and at least one mitochondrial targeting sequence; binding and entering of the vector into mitochondria; and, introducing nucleic acid molecules into mitochondria.

In another preferred embodiment, the mitochondrial gene of interest is introduced into a patient by obtaining cells from a patient; culturing the cells ex vivo with the composition encoding the mitochondrial gene and mitochondrial targeting sequences; wherein the composition is targeted to the mitochondria and the desired gene is expressed in the mitochondria and re-administering the cells to the patient. The cells can be obtained either from the patient or from a donor. The cells can be obtained from organs, skin, tissues, muscles and bone marrow. The cells are preferably autologous, however they can be HLA-compatible or partially HLA matched.

In one embodiment, the cells are stem cells and are obtained from bone marrow.

In another preferred embodiment, a method of introducing a nucleic acid molecule into a mitochondrion in vitro, comprises culturing cells with a composition comprising a vector encoding at least one mitochondrial gene wherein said gene is operably linked to a mitochondrial promoter, at least one mitochondrial targeting sequence; binding and entering of the vector into mitochondria; expressing the mitochondrial gene in mitochondria; and, introducing the nucleic acid molecule into a mitochondrion.

In another preferred embodiment, a mitochondrial gene can be silenced, down-regulated or up-regulated. For example, the delivery of a nucleic acid in such cases is in the form of siRNA's which are directed to a gene to be silenced, a promoter, enhancer etc which can modulate gene expression.

Inhibition of gene expression may be quantified by measuring either the endogenous target RNA or the protein produced by translation of the target RNA. Techniques for quantifying RNA and proteins are well known to one of ordinary skill in the art. In certain preferred embodiments, gene expression is inhibited by at least 10%, preferably by at least 33%, more preferably by at least 50%, and yet more preferably by at least 80%. In particularly preferred embodiments, of the invention gene expression is inhibited by at least 90%, more preferably by at least 95%, or by at least 99% up to 100% within cells in the organism. Note that although in certain embodiments of the invention inhibition occurs in substantially all cells of the subject, in other preferred embodiments inhibition occurs in only a subset of cells expressing the heterologous gene.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 6B is a histogram showing a 48% increase in the rate of ATP synthesis in LHON cybrids infected with the mito-targeted AAV (8 gfp) expressing wild-type ND4 relative to LHON cells infected with the same AAV vector lacking the MTS (cont), $p<0.05$.

DETAILED DESCRIPTION

Figure 1:
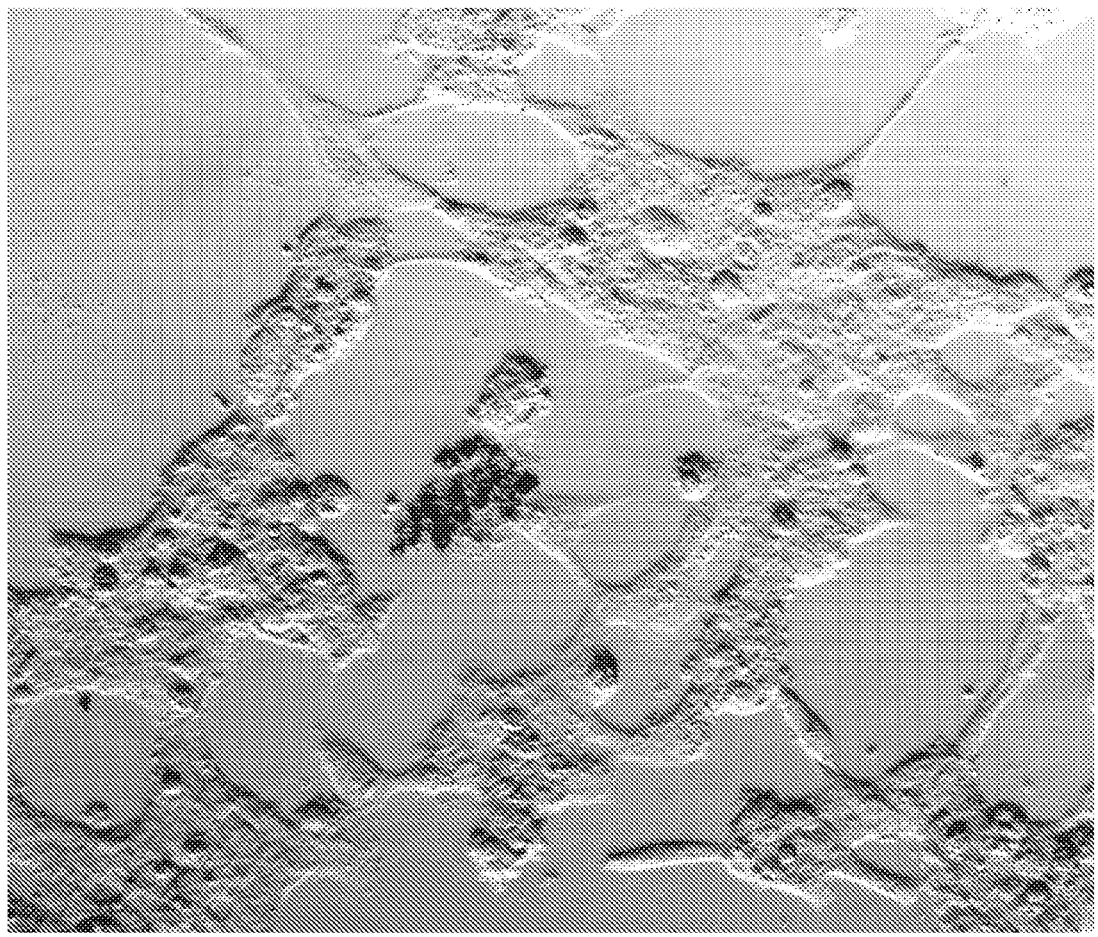
FIG. 1 is an electron microscope scan showing that A20 immunogold recognizes fully assembled AAV virions (arrow) in the mitochondria.
Figure 2:
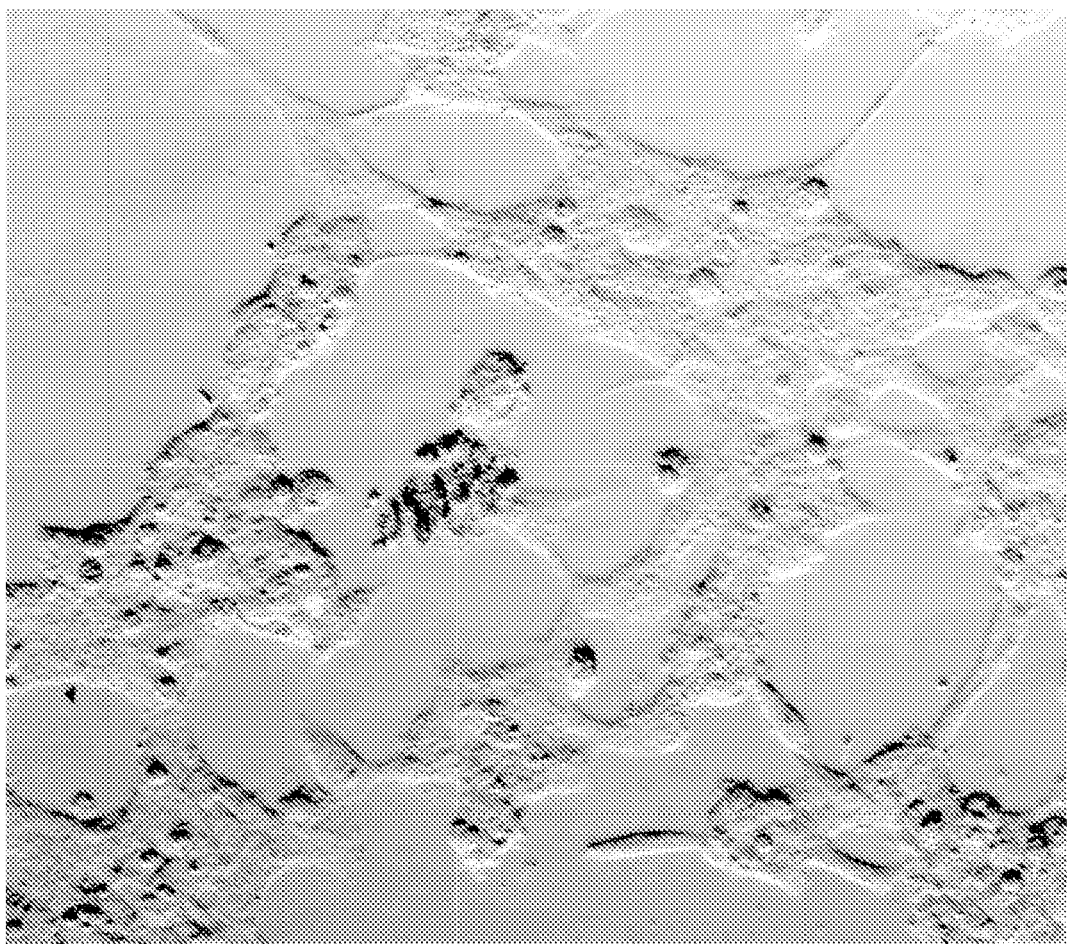
FIG. 2 is an electron microscope scan showing that GFP and A20 immunogold co-localization indicating fully assembled virus is imported into the mitochondria.
Figure 3:
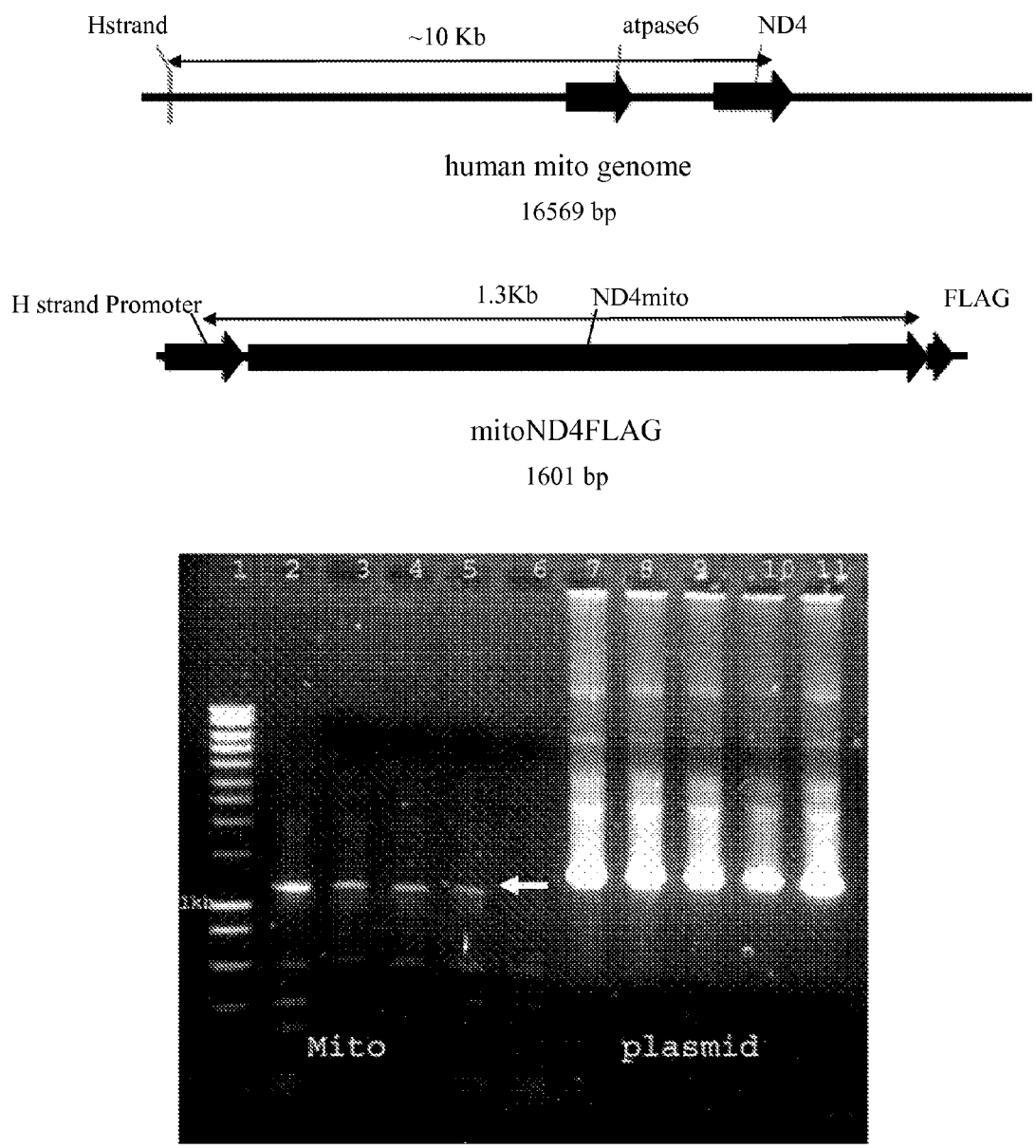
FIG. 3 is a scan of an agarose gel showing PCR product of mtDNA isolated from cells infected with mitochondrially targeted AAV containing the H strand promoter driving expression of the ND4 subunit gene in the mitochondrial genetic code in Lanes 2-6 (arrow). Amplification of plasmid DNA is shown in lanes 7 to 11.
Figure 4:
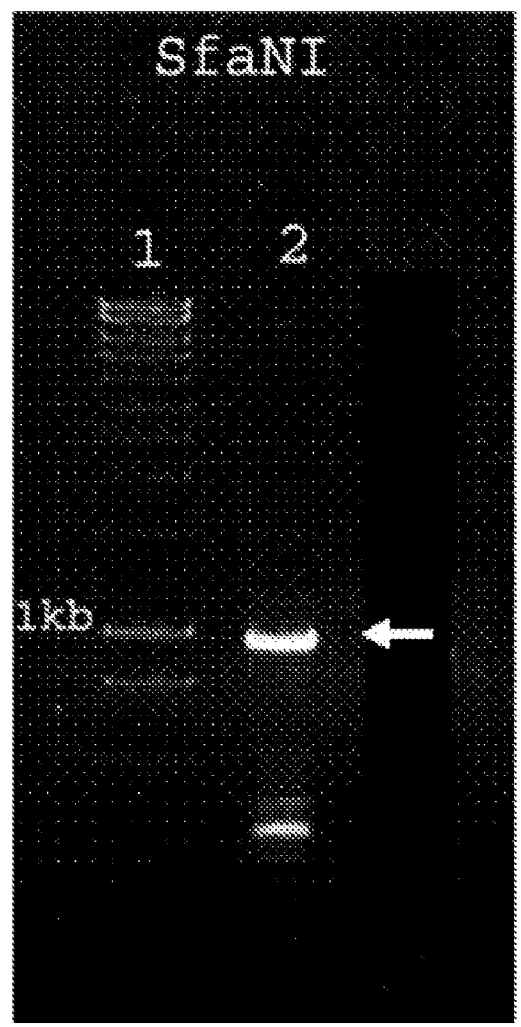
FIG. 4 is a scan of an SfaNI digest showing 915 bp band (arrow) indicating the presence of wild-type mitochondrial ND4 DNA in mito-AAV transfected LHON cybrids homoplasmic for G11778A mtDNA. The G11778A mutation eliminates an SfaNI site at the ND4 locus shown above the digest.
Figure 5:
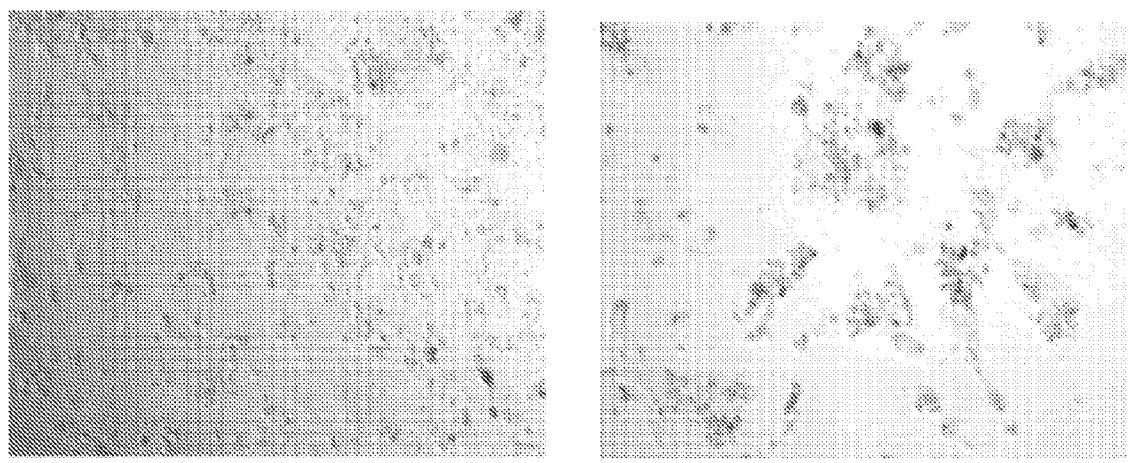
FIG. 5 are micrographs of live cell cultures showing healthy appearing LHON cybrids infected with the mito-targeted AAV expressing wild-type ND4 even after 5 days of growth in galactose (left). Homoplasmic G11778A cells infected with the AAV lacking the MTS are dead or dying (right)
Figure 6A:
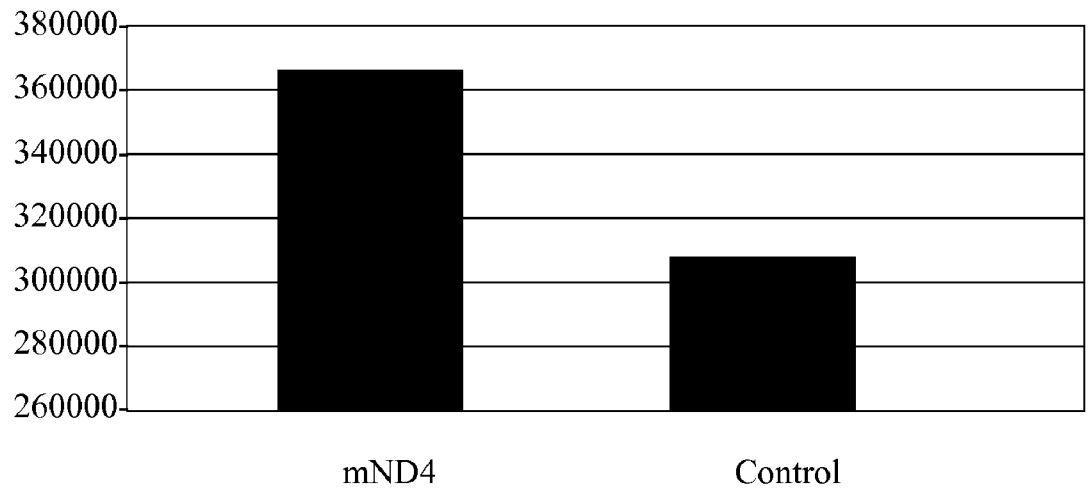
FIGS. 6A and 6B are graphs showing AAV mitoND4 rescue. After 48 hours of growth in galactose we found a 19% increase in cell survival ($p<0.05$) relative to controls, the cybrid cells infected with the same ND4 gene but in a virus without the MTS attached to the GFP expressing VP2.
Figure 6B:
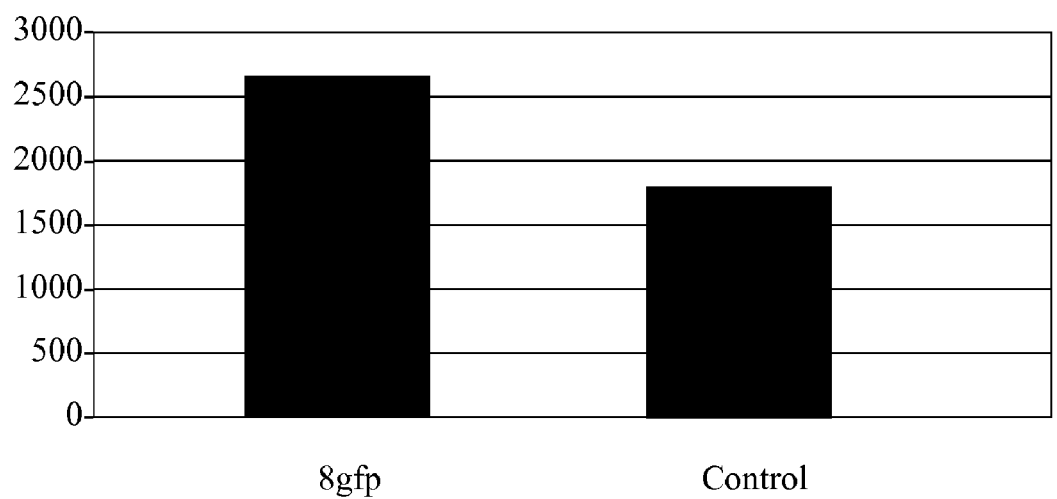
Figure 7:
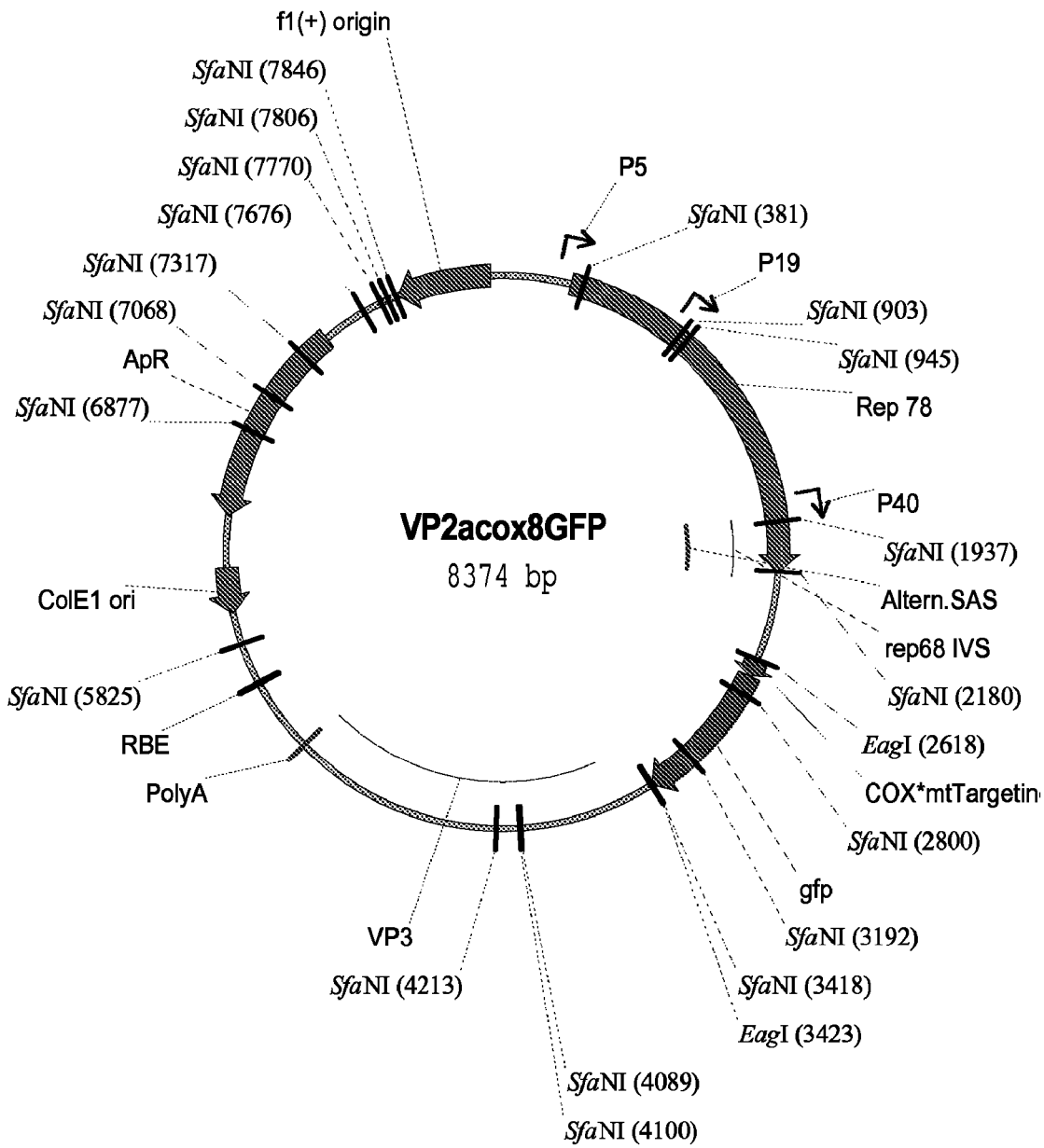
FIG. 7 is a schematic illustration showing COX8 MTS-AAV expressing GFP plasmid.

Vectors comprising mitochondrial genes and targeting sequences are directed into mitochondria. The mitochondrial genes are expressed in the mitochondria. Methods of transducing the mitochondria are described.

Definitions

Prior to setting forth the invention, the following definitions are provided:

As used herein, the singular forms "a", "an" and "the" include plural referents unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

The term "DNA construct" and "vector" are used herein to mean a purified or isolated polynucleotide that has been artificially designed and which comprises at least two nucleotide sequences that are not found as contiguous nucleotide sequences in their natural environment.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures. Single or double stranded DNA or RNA and linear or circular. Single stranded DNA can be used for expression and circular RNA can also be used for expression.

As used interchangeably herein, the terms "oligo-nucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The phrase "having a length of N bases" or "having a length of N nucleotides" is used herein to describe lengths along a single nucleotide strand, of a nucleic acid molecule, consisting of N individual nucleotides.

As used herein, the term "bind", refers to an interaction between the bases of an oligonucleotide which is mediated through base-base hydrogen bonding. One type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix.

As used herein, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$ where n is from 1 to about 10, and other substituents having similar properties.

As used herein, the term "administering a molecule to a cell" (e.g., an expression vector, nucleic acid, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A "vector" (sometimes referred to as gene delivery or gene transfer "vehicle") refers to a macromolecule or complex of molecules comprising a polynucleotide to be delivered to a host cell, either in vitro or in vivo. The "vector" can be any nucleic acid- and/or viral-based technique used to deliver a desired nucleic acid. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques,* 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

By "nucleic acid" is meant both RNA and DNA including: cDNA, genomic DNA, plasmid DNA or condensed nucleic acid, nucleic acid formulated with cationic lipids, nucleic acid formulated with peptides, cationic polymers, RNA or mRNA. In a preferred embodiment, the nucleic acid administered is a plasmid DNA which constitutes a "vector." The nucleic acid can be, but is not limited to, a plasmid DNA vector with a eukaryotic promoter which expresses a protein with potential therapeutic action.

As used herein, the term a "plasmid" refers to a construct made up of genetic material (i.e., nucleic acids). It includes genetic elements arranged such that an inserted coding sequence can be transcribed in eukaryotic cells. In this case, a preferred embodiment comprises a mitochondrial targeting sequence, a mitochondrial gene operably linked to a mitochondrial promoter. Also, while the plasmid may include a sequence from a viral nucleic acid, such viral sequence preferably does not cause the incorporation of the plasmid into a viral particle, and the plasmid is therefore a non-viral vector. Preferably, a plasmid is a closed circular DNA molecule. The enhancer/promoter region of an expression plasmid will determine the levels of expression. Most of the gene expression systems designed for high levels of expression contain the intact human cytomegalovirus (CMV) immediate early enhancer/promoter sequence. However, down-regulation of the CMV promoter over time has been reported in tissues. The hypermethylation of the CMV promoter, as observed when incorporated into retroviral vectors, has not been observed for episomal plasmids in vivo. Nevertheless, the CMV promoter silencing could be linked to its sensitivity to reduced levels of the transcription factor NF-κB. The activity of the CMV promoter has also been shown to be attenuated by various cytokines including interferons ($\alpha$ and $\beta$), and tumor necrosis factor (TNF-$\alpha$). In order to prolong expression in vivo and ensure specificity of expression in desired tissues, tissue-specific enhancer/promoters have been incorporated in expression plasmids. The chicken skeletal alpha actin promoter has been shown to provide high levels of expression (equivalent to the ones achieved with a CMV-driven construct) for several weeks in non-avian striated muscles.

Additional genetic sequences in the expression plasmids can be added to influence the stability of the messenger RNA (mRNA) and the efficiency of translation. The 5' untranslated region (5' UTR) is known to effect translation and it is located between the cap site and the initiation codon. The 5' UTR should ideally be relatively short, devoid of strong secondary structure and upstream initiation codons, and should have an initiation codon AUG within an optimal local context. The 5' UTR can also influence RNA stability, RNA processing and transcription. In order to maximize gene expression by ensuring effective and accurate RNA splicing, one or more introns can be included in the expression plasmids at specific locations. The possibility of inefficient and/or inaccurate splicing can be minimized by using synthetic introns that have idealized splice junction and branch point sequences that match the consensus sequence. Another important sequence within a gene expression system is the 3' untranslated region (3' UTR), a sequence in the mRNA that extends from the stop codon to the poly(A) addition site. The 3' UTR can influence mRNA stability, translation and intracellular localization. The skeletal muscle .alpha.-actin 3' UTR has been shown to stabilize mRNA in muscle tissues thus leading to higher levels of expression as compared to other 3' UTR. This 3'

UTR appears to induce a different intracellular compartmentalization of the produced proteins, preventing the effective trafficking of the proteins to the secretory pathway and favoring their perinuclear localization. One of the attractive features of plasmid expression systems is the possibility to express multiple genes from a single construct.

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" gene products, found in many viral genomes, are gene products encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain gene products encoding the missing functions which can be supplied in trans). For example, such packaging gene products can be stably integrated into a replicon of the packaging cell line or they can be introduced by transfection with a "packaging plasmid" or helper virus carrying gene products encoding the missing functions.

A "detectable marker gene" is a gene that allows cells carrying the gene to be specifically detected (e.g., distinguished from cells which do not carry the marker gene). A large variety of such marker gene products are known in the art. Preferred examples thereof include detectable marker gene products which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker gene products have been described, including bifunctional (i.e. positive/negative) markers (see, e.g., WO 92/08796, published May 29, 1992, and WO 94/28143, published Dec. 8, 1994). Such marker gene products can provide an added measure of control that can be advantageous in gene therapy contexts.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented.

As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, "allogeneic" is used to refer to immune cells derived from non-self major histocompatibility complex donors. HLA haplotypes/allotypes vary from individual to individual and it is often helpful to determine the individual's HLA type. The HLA type may be determined via standard typing procedures.

As will be recognized by those in the art, the term "host compatible" or "autologous" cells means cells that are of the same or similar haplotype as that of the subject or "host" to which the cells are administered, such that no significant immune response against these cells occurs when they are transplanted into a host.

As used herein, "partially-mismatched HLA", refers to HLA types that are between about 20% to about 90% compatible to the host's HLA type.

Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). Bone marrow derived stem cells contain two well-characterized types of stem cells. Mesenchymal stem cells (MSC) normally form chondrocytes and osteoblasts. Hematopoietic stem cells (HSC) are of mesodermal origin that normally give rise to cells of the blood and immune system (e.g., erythroid, granulocyte/macrophage, magakaryocite and lymphoid lineages). In addition, hematopoietic stem cells also have been shown to have the potential to differentiate into the cells of the liver (including hepatocytes, bile duct cells), lung, kidney (e.g., renal tubular epithelial cells and renal parenchyma), gastrointestinal tract, skeletal muscle fibers, astrocytes of the CNS, Purkinje neurons, cardiac muscle (e.g., cardiomyocytes), endothelium and skin.

As used herein, "mitochondrial related disorders" related to disorders which are due to abnormal mitochondria such as for example, a mitochondrial genetic mutation, enzyme pathways etc. Examples of disorders include and are not limited to: loss of motor control, muscle weakness and pain, gastrointestinal disorders and swallowing difficulties, poor growth, cardiac disease, liver disease, diabetes, respiratory complications, seizures, visual/hearing problems, lactic acidosis, developmental delays and susceptibility to infection. The mitochondrial abnormalities give rise to "mitochondrial diseases" which include, but not limited to: AD: Alzheimer's Disease; ADPD: Alzheimer's Disease and Parkinsons's Disease; AMDF: Ataxia, Myoclonus and Deafness CIPO: Chronic Intestinal Pseudoobstruction with myopathy and Opthalmoplegia; CPEO: Chronic Progressive External Opthalmoplegia; DEAF: Maternally inherited DEAFness or aminoglycoside-induced DEAFness; DEMCHO: Dementia and Chorea; DMDF: Diabetes Mellitus & DeaFness; Exercise Intolerance; ESOC: Epilepsy, Strokes, Optic atrophy, & Cognitive decline; FBSN: Familial Bilateral Striatal Necrosis; FICP: Fatal Infantile Cardiomyopathy Plus, a MELAS-associated cardiomyopathy; GER: Gastrointestinal Reflux; KSS Kearns Sayre Syndrome LDYT: Leber's hereditary optic neuropathy and DYsTonia; LHON: Leber Hereditary Optic Neuropathy; LIMM: Lethal Infantile Mitochondrial Myopathy; MDM: Myopathy and Diabetes Mellitus; MELAS: Mitochondrial Encephalomyopathy, Lactic Acidosis, and Stroke-like episodes; MEPR: Myoclonic Epilepsy and Psychomotor Regression; MERME: MERRF/MELAS overlap disease; MERRF: Myoclonic Epilepsy and Ragged Red Muscle Fibers; MHCM: Maternally Inherited Hypertrophic CardioMyopathy; MICM: Maternally Inherited Cardiomyopathy; MILS: Maternally Inherited Leigh Syndrome; Mitochondrial Encephalocardiomyopathy; Mitochondrial Encephalomyopathy; MM: Mitochondrial Myopathy; MMC: Maternal Myopathy and Cardiomyopathy; Multisystem Mitochondrial Disorder (myopathy, encephalopathy, blindness, hearing loss, peripheral neuropathy); NARP: Neurogenic muscle weakness, Ataxia, and Retinitis Pigmentosa; alternate phenotype at this locus is reported as Leigh Disease; NIDDM: Non-Insulin Dependent Diabetes Mellitus; PEM: Progressive Encephalopathy; PME: Progressive Myoclonus Epilepsy; RTT: Rett Syndrome; SIDS: Sudden Infant Death Syndrome.

Adeno-Associated Viruses.

In a preferred embodiment, a composition comprises a nucleic acid encoding a viral vector; mitochondrial promoters; a mitochondrial gene and a mitochondrial targeting sequence; fragments and variants thereof.

In a preferred embodiment, the vector is an adeno-associated virus.

In one aspect, the mitochondrial targeting sequence is inserted into the AAV capsid open reading frame (cap ORF). However, the mitochondrial targeting sequences can be inserted into any region of a vector; insert single or multiple copies of the same or different targeting sequences.

In another preferred embodiment, the mitochondrial gene is operably linked to the mitochondrial promoter and inserted into the AAV vector backbone.

In another preferred embodiment, the AAV is selected from the group consisting of AAV-1 to AAV-9 serotypes. The AAV genome can comprise Rep and Cap genes from other AAV serotypes and/or the AAV can be pseudotyped.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

In some embodiments, an AAV vector is a self-complementary AAV (scAAV) vector containing a double-stranded vector genome. Such a vector is typically generated by deleting the terminal resolution site from one rAAV ITR in an rAAV vector construct, thereby preventing initiation of replication at the mutated end. When propagated in a host cell, such a construct generates single-stranded, inverted-repeat genomes having a wild-type ITR at each end and a mutated ITR in the middle. scAAV vectors may be particularly useful for gene transfer to the mitochondria, because the incubation time needed to attain gene expression from a single-stranded rAAV vector is typically 7 weeks, a period of time that is too long for some clinical applications. scAAV vectors enter cells as double-stranded DNA, eliminating the step of second-strand synthesis, the rate-limiting step for gene expression of single-stranded rAAV vectors.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques. The invention also relates, therefore, to an AAV-derived recombinant virus whose genome encompasses a sequence encoding a nucleic acid encoding a mitochondrial gene and a mitochondrial targeting sequence, flanked by the AAV ITRs. The invention also relates to a plasmid encompassing a sequence encoding a nucleic acid encoding a desired gene flanked by two ITRs from an AAV. Such a plasmid can be used as it is for transferring the nucleic acid sequence, with the plasmid, where appropriate, being incorporated into a liposomal vector (pseudo-virus).

Examples of mitochondrial related diseases which can be treated using the compositions of the invention comprise: Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Opthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Opthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young, and MNGIE.

In another preferred embodiment, the mitochondrial targeting sequences comprise nucleic acid molecules encoding: cytochrome c oxidase (COX); ATP synthase; subunit c of human ATP synthase (ATPc); ATP synthase; hexokinase I, amine oxidase (flavin-containing) A, hexokinase IV, pancreatic beta cell form, peripheral benzodiazepine receptor-related protein, metaxin 2, putative mitochondrial outer membrane protein import receptor (hTOM), glutathione transferase; voltage-dependent anion channel 2 (outer mitochondrial membrane protein porin), hexokinase IV, cytochrome b5, peripheral benzodiazepine receptor, germ cell kinase anchor S-AKAP84, A kinase anchor protein, carnitine O-palmitoyltransferase I precursor, hexokinase II, amine oxidase (flavin-containing) B, long-chain-fatty-acid—CoA ligase 2, long-chain-fatty-acid—CoA ligase 1 (palmitoyl-CoA ligase), voltage-dependent anion channel 1, metaxin 1, Human putative outer mitochondrial membrane 34 kDa translocase hTOM34, voltage-dependent anion channel 4 (outer mitochondrial membrane protein porin), cytochrome-b5 reductase, voltage-dependent anion channel 3 (outer mitochondrial membrane protein porin), Mitochondrial import receptor subunit TOM20 homolog (Mitochondrial 20 kd outer membrane protein) (Outer mitochondrial membrane receptor TOM20), and tumorous imaginal discs homolog precursor (HTID-1); fragments and variants thereof.

Other Vectors

In other preferred embodiments, vectors delivering gene payloads for the treatment of mitochondrial disorders comprise viral and non-viral vectors are used to transduce the mitochondria.

Retrovirus vectors: In another preferred embodiment the mitochondrial genes can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. *Genet. Eng.* 7 (1985) 235; McCormick, *BioTechnology* 3 (1985) 689; International Patent Publication No. WO 95/07358, published Mar. 16, 1995, by Webster, K. A., Kubasiak, L. A., Prentice, H. and Bishopric, N. H.: Stable germline transmission of a hypoxia-activated molecular gene switch. From the double helix to molecular medicine, (ed. W. J. Whelan et al.), Oxford University Press, (2003); and Kuo et al., 1993, *Blood* 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., *J. Virol.* 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus. Targeted gene delivery is described in International Patent Publication WO 95/28494, published October 1995.

Lentiviral Vectors: lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., 1999, *Frontiers in Bioscience* 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. HIV-1 is preferred.

Autonomous parvoviruses are small DNA viruses that replicate autonomously in rapidly dividing cells. The genomes of autonomous parvoviruses do not integrate, at least not at a detectable level. Autonomous parvovirus genomes are single-stranded DNA molecules about 5 kilobases (kb) in size. The genomes are organized such that the NS gene encoding the nonstructural polypeptides NS1 and NS2 is located on the left side of the genome and the VP gene encoding the structural polypeptides required for capsid formation are on the right side of the genome. Expression of the nonstructural polypeptides is controlled by a transcription control sequence called P4 in most parvoviruses, which is located at about map unit position 4 of the genome (assuming the entire genome is 100 map units and numbering is from left to right). Expression of the structural polypeptides is controlled by a transcription control sequence called P38, P39 or P40 in most parvoviruses, which is located at about map unit position 38 to about 40, depending on the autonomous parvovirus. NS1 serves as a trans-activator of the latter transcription control sequence. NS1 is also essential for virus replication and appears to be the primary mediator of parvovirus cytotoxicity, particularly against tumor cells. Autonomous parvovirus genomes also have inverted repeat sequences (i.e., palindromes) at each end which contain essential signals for replication and encapsidation of the virus. There have been several studies on the mechanistics of autonomous parvovirus replication, gene expression, encapsidation, and cytotoxicity. See, for example, Sinkovics, pp. 1281-1290, 1989, Anticancer Res., Vol 9.

Suitable autonomous parvovirus nucleic acid sequences include, but are not limited to, LuIII parvovirus (LuIII), minute virus of mice (MVM; e.g., MVMi and MVMp), hamster parvovirus (e.g., HD, feline panleukopenia virus, canine parvovirus, porcine parvovirus, latent rat virus, mink enteritis virus, human parvovirus (e.g., B19), bovine parvovirus, and Aleutian mink disease parvovirus nucleic acid sequences. LuIII parvovirus is a parvovirus of unknown origin that was isolated as a contaminant of a substrain of human permanent cell line Lu106. The LuIII parvovirus exhibits high infectivity.

Non-viral Vectors: alternatively, the vector can be introduced in vivo as nucleic acid free of transfecting excipients, or with transfection facilitating agents, e.g., lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Ulmer et al., *Science* 259:1745-1748 (1993)]. The use of cationic lipids may promote encapsulation of negatively charged nucleic acids, and also promote fusion with negatively charged cell membranes [Feigner and Ringold, *Science* 337:387-388 (1989)]. Particularly useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Naked DNA vectors can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963-967 (1992); Wu and Wu, *J. Biol. Chem.* 263: 14621-14624 (1988); Williams et al., *Proc. Natl. Acad. Sci. USA* 88:2726-2730 (1991)]. Receptor-mediated DNA delivery approaches can also be used [Curiel et al., *Hum. Gene Ther.* 3:147-154 (1992); Wu and Wu, *J. Biol. Chem.* 262: 4429-4432 (1987)]. Methods for formulating and administering naked DNA to mammalian muscle tissue are disclosed in U.S. Pat. Nos. 5,580,859 and 5,589,466, the contents of which are incorporated herein by reference.

Mitochondrial Targeting

Mitochondria contain the molecular machinery for the conversion of energy from the breakdown of glucose into adenosine triphosphate (ATP). The energy stored in the high energy phosphate bonds of ATP is then available to power cellular functions. Mitochondria are mostly protein, but some lipid, DNA and RNA are present. These generally spherical organelles have an outer membrane surrounding an inner membrane that folds (cristae) into a scaffolding for oxidative phosphorylation and electron transport enzymes. Most mitochondria have flat shelf-like cristae, but those in steroid secreting cells may have tubular cristae. The mitochondrial matrix contains the enzymes of the citric acid cycle, fatty acid oxidation and mitochondrial nucleic acids.

Mitochondrial DNA is double stranded and circular. Mitochondrial RNA comes in the three standard varieties; ribosomal, messenger and transfer, but each is specific to the mitochondria. Some protein synthesis occurs in the mitochondria on mitochondrial ribosomes that are different than cytoplasmic ribosomes. Other mitochondrial proteins are made on cytoplasmic ribosomes with a signal peptide that directs them to the mitochondria. The metabolic activity of the cell is related to the number of cristae and the number of mitochondria within a cell. Cells with high metabolic activity, such as heart muscle, have many well developed mitochondria. New mitochondria are formed from preexisting mitochondria when they grow and divide. The inner membranes of mitochondria contain a family of proteins of related sequence and structure that transport various metabolites across the membrane. Their amino acid sequences have a tripartite structure, made up of three related sequences about 100 amino acids in length. The repeats of one carrier are related to those present in the others and several characteristic sequence features are conserved throughout the family.

Targeting of specific polynucleotides to organelles can be accomplished by modifying the disclosed compositions to express specific organelle targeting signals. These sequences target specific organelles, but in some embodiments the interaction of the targeting signal with the organelle does not occur through a traditional receptor:ligand interaction. The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure.

In one embodiment, the nucleic acid molecules expressing a mitochondrial targeting signal can encode amino acids comprising at least two, preferably 5-15, most preferably about 11 charged groups. In another embodiment, the targeting signal can contain a series of charged groups that cause the targeting signal to be transported into an organelle either against or down an electromagnetic potential gradient. Suitable charged groups are groups that are charged under intracellular conditions such as amino acids with charged functional groups, amino groups, nucleic acids, and the like. Mitochondrial localization/targeting signals generally consist of a leader sequence of highly positively charged amino acids. This allows the protein to be targeted to the highly negatively charged mitochondria. Unlike receptor:ligand approaches that rely upon stochastic Brownian motion for the ligand to approach the receptor, the mitochondrial localization signal of some embodiments is drawn to mitochondria because of charge.

In order to enter the mitochondria, a protein generally must interact with the mitochondrial import machinery, consisting of the Tim and Tom complexes (Translocase of the Inner/Outer Mitochondrial Membrane). With regard to the mitochondrial targeting signal, the positive charge draws the linked protein to the complexes and continues to draw the protein into the mitochondria. The Tim and Tom complexes allow the proteins to cross the membranes. Accordingly, one embodiment of the present disclosure delivers compositions of the present disclosure to the inner mitochondrial space utilizing a positively charged targeting signal and the mitochondrial import machinery. In another embodiment, PTD-linked polypeptides containing a mitochondrial localization signal do not seem to utilize the TOM/TIM complex for entry into the mitochondrial matrix, see Del Gaizo et al. (2003) *Mol Genet Metab.* 80(1-2):170-80.

Mitochondrial mutations are the cause of maternally inherited diseases affecting tissues that primarily rely on oxidative energy metabolism, usually the central and peripheral nervous system, the heart and the skeletal muscles. The multi-systemic nature of these diseases is reflected in the acronyms by which they are sometimes named: for example, MERRF, for myoclonic epilepsy with ragged red fibers; MELAS, for mitochondrial encephalopathy-lactic acidosis and stroke-like episodes; NARP, for neuropathy, ataxia and retinitis pigmentosa. Large deletions or rearrangements of DNA are the cause of some mitochondrial diseases, such as Kearns-Sayre syndrome that leads to opthalmoplegia, pigmentary degeneration of the retina and cardiomyopathy. Almost all of these cases are sporadic and they are believed to be caused by a heavy burden of deleted mtDNA in affected tissues of a heteroplasmic individual during fetal development. In addition to loss or alteration of protein coding genes, MERRF and MELAS mutations alter tRNA genes, though MELAS mutations in tRNALeu(UUR) may also affect RNA processing. Patients are frequently heteroplasmic for the mutation, explaining the fact that symptoms may be delayed until adolescence or even adulthood.

Given the importance of mitochondria in human disease, cell proliferation, cell death, and aging, embodiments of the present disclosure also encompasses the manipulation of the mitochondrial genome to supply the means by which known mitochondrial diseases (LHON, MELAS, etc.) and putative mitochondrial diseases (aging, Alzheimer's, Parkinson's, Diabetes, Heart Disease) can be treated.

TABLE 1

Specific disorders with mtDNA mutations

| mtDNA Point mutations |
| --- |
| Cardiomyopathy |
| Leber's optic neuropathy |
| Leigh's syndrome |
| MELAS |
| MERRF |
| NARP/MILS |
| Single deletion or duplication |
| Ataxia, Leukodystrophy |
| Diabetes: Maternal inheritance |
| Kearns-Sayre |
| Pearson's |
| PEO: Sporadic |
| Multiple deletions |
| Aging |
| Myositis |
|   Inclusion body |
|     COX- muscle fibers |
| MNGIE |
| PEO |
| Wolfram |
| Depletion of mtDNA |
| Infantile myopathy |
|   Fatal |
|   "Later-onset" |
| AZT treatment |
| Several types of mtDNA defect |
| Deafness |
| Diabetes |
| External ophthalmoplegia (PEO) |
|   Sporadic |
|   Maternal |

TABLE 1-continued

Specific disorders with mtDNA mutations

Dominant
Recessive
Leigh's
Myopathy
Rhabdomyolysis
Sensory neuropathy
Systemic disorders The examples of disorders with mtDNA mutations are shown in Table 1. This list is not meant to be exhaustive but provides some examples of diseases which can be treated using the compositions of the invention.

In one embodiment, a normal gene is introduced into mitochondria to compensate for the mutated mitochondrial gene giving rise to a disorder. For example, a normal ND4 gene. The following table, Table 2, is illustrative of mitochondrial DNA mutations and the mitochondrial disorders which result.

In one embodiment, the mutated genes for which a normal gene is introduced and expressed in the mitochondria comprise mtDNA insertions, deletions, substitutions, inversions, point mutations and the like. Examples of mutations and loci are shown in Table 2.

| Locus | Disease | Allele | RNA |
|---|---|---|---|
| MT-TF | *Mitochondrial Myopathy | T582C | tRNA Phe |
| MT-TF | *MELAS/MM & EXIT | G583A | tRNA Phe |
| MT-TF | *Myoglobinuria | A606G | tRNA Phe |
| MT-TF | *Tubulointerstitial nephritis | A608G | tRNA Phe |
| MT-TF | *MERRF | G611A | tRNA Phe |
| MT-TF | *MM | T618C | tRNA Phe |
| MT-TF | *EXIT & Deafness | G622A | tRNA Phe |
| MT-RNR1 | *DEAF | A827G | 12S rRNA |
| MT-RNR1 | *DEAF | T961C | 12S rRNA |
| MT-RNR1 | *DEAF | T961delT + C(n)ins | 12S rRNA |
| MT-RNR1 | *DEAF | T961insC | 12S rRNA |
| MT-RNR1 | *DEAF | T1005C | 12S rRNA |
| MT-RNR1 | *SNHL | T1095C | 12S rRNA |
| MT-RNR1 | *DEAF | A1116G | 12S rRNA |
| MT-RNR1 | *DEAF | C1494T | 12S rRNA |
| MT-RNR1 | *DEAF | A1555G | 12S rRNA |
| MT-TV | *AMDF | G1606A | tRNA Val |
| MT-TV | *Leigh Syndrome | C1624T | tRNA Val |
| MT-TV | *MELAS | G1642A | tRNA Val |
| MT-TV | *Adult Leigh Syndrome | G1644T | tRNA Val |
| MT-TV | *Movement Disorder | T1659C | tRNA Val |
| MT-RNR2 | *Rett Syndrome | C2835T | 16S rRNA |
| MT-RNR2 | *MELAS | C3093G | 16S rRNA |
| MT-RNR2 | *ADPD | G3196A | 16S rRNA |
| MT-TL1 | *MM | G3242A | tRNA Leu (UUR) |
| MT-TL1 | *MELAS | A3243G | tRNA Leu (UUR) |
| MT-TL1 | *DM/DMDF | A3243G | tRNA Leu (UUR) |
| MT-TL1 | *CPEO/MM | A3243G | tRNA Leu (UUR) |
| MT-TL1 | *MM | A3243T | tRNA Leu (UUR) |
| MT-TL1 | *MELAS | G3244A | tRNA Leu (UUR) |
| MT-TL1 | *KSS | G3249A | tRNA Leu (UUR) |
| MT-TL1 | *MM/CPEO | T3250C | tRNA Leu (UUR) |
| MT-TL1 | *MM | A3251G | tRNA Leu (UUR) |
| MT-TL1 | *MELAS | A3252G | tRNA Leu (UUR) |
| MT-TL1 | *MM | C3254G | tRNA Leu (UUR) |
| MT-TL1 | *CPEO | C3254T | tRNA Leu (UUR) |
| MT-TL1 | *MERRF/KSS overlap | G3255A | tRNA Leu (UUR) |
| MT-TL1 | *MELAS | C3256T | tRNA Leu (UUR) |
| MT-TL1 | *MELAS/Myopathy | T3258C | tRNA Leu (UUR) |
| MT-TL1 | *MMC | A3260G | tRNA Leu (UUR) |
| MT-TL1 | *DM | T3264C | tRNA Leu (UUR) |
| MT-TL1 | *MELAS | T3271C | tRNA Leu (UUR) |
| MT-TL1 | *DM | T3271C | tRNA Leu (UUR) |
| MT-TL1 | *PEM | T3271delT | tRNA Leu (UUR) |
| MT-TL1 | *Ocular myopathy | T3273C | tRNA Leu (UUR) |
| MT-TL1 | *LHON | C3275A | tRNA Leu (UUR) |
| MT-TL1 | *Myopathy | A3280G | tRNA Leu (UUR) |
| MT-TL1 | *Myopathy | A3288G | tRNA Leu (UUR) |
| MT-TL1 | *MELAS | T3291C | tRNA Leu (UUR) |
| MT-TL1 | *MM | A3302G | tRNA Leu (UUR) |
| MT-TL1 | *MMC | C3303T | tRNA Leu (UUR) |
| MT-TI | *MM | A4267G | tRNA Ile |
| MT-TI | *FICP | A4269G | tRNA Ile |
| MT-TI | *CPEO/Motor Neuron Disease | T4274C | tRNA Ile |
| MT-TI | *Varied familial presentation | G4284A | tRNA Ile |
| MT-TI | *CPEO | T4285C | tRNA Ile |
| MT-TI | *Progressive Encephalopathy | T4290C | tRNA Ile |
| MT-TI | *Hypomagnesemic Metabolic Syndrome | T4291C | tRNA Ile |
| MT-TI | *MHCM | A4295G | tRNA Ile |
| MT-TI | *CPEO/MS | G4298A | tRNA Ile |
| MT-TI | *MICM | A4300G | tRNA Ile |
| MT-TI | *CPEO | G4309A | tRNA Ile |
| MT-TI | *FICP | A4317G | tRNA Ile |
| MT-TI | *Mitochondrial Encephalocardiomyopathy | C4320T | tRNA Ile |
| MT-TQ | *Encephalopathy/MELAS | G4332A | tRNA Gln |
| MT-TQ | *ADPD/Hearing Loss & Migraine | T4336C | tRNA Gln |
| MT-TQ | *Myopathy | T4370AT | tRNA Gln |
| MT-TQ | *LHON | A4381G | tRNA Gln |
| MT-TM | *MM | T4409C | tRNA Met |
| MT-TM | *LHON modulator | A4435G | tRNA Met |
| MT-TM | *Myopathy | G4450A | tRNA Met |
| MT-TW | *MM | G5521A | tRNA Trp |
| MT-TW | *Gastrointestinal Syndrome | G5532A | tRNA Trp |
| MT-TW | *Leigh Syndrome | A5537insT | tRNA Trp |
| MT-TW | *Encephalomyopathy | G5540A | tRNA Trp |
| MT-TW | *DEMCHO | G5549A | tRNA Trp |
| MT-TA | *Myopathy | G5591A | tRNA Ala |
| MT-TA | *CPEO | T5628C | tRNA Ala |
| MT-TN | *CPEO/MM | T5692C | tRNA Asn |
| MT-TN | *CPEO/MM | G5698A | tRNA Asn |
| MT-TN | *CPEO/MM | G5703A | tRNA Asn |
| MT-TC | *Mitochondrial Encephalopathy | T5814C | tRNA Cys |
| MT-TY | *FSGS/Mitochondrial Cytopathy | A5843G | tRNA Tyr |
| MT-TY | *EXIT | T5874G | tRNA Tyr |
| MT-TS1 precursor | *DEAF | A7445C | tRNA Ser (UCN) precursor |
| MT-TS1 precursor | *SNHL | A7445G | tRNA Ser (UCN) precursor |
| MT-TS1 | *PEM/AMDF | C7472insC | tRNA Ser (UCN) |
| MT-TS1 | *MM | T7480G | tRNA Ser (UCN) |
| MT-TS1 | *MM/EXIT | G7497A | tRNA Ser (UCN) |
| MT-TS1 | *SNHL | T7510C | tRNA Ser (UCN) |
| MT-TS1 | *SNHL | T7511C | tRNA Ser (UCN) |
| MT-TS1 | *PEM/MERME | T7512C | tRNA Ser (UCN) |
| MT-TD | *MEPR | A7543G | tRNA Asp |
| MT-TK | *DMDF/MERRF/HCM | A8296G | tRNA Lys |
| MT-TK | *Encephalopathy | C8302T | tRNA Lys |
| MT-TK | *MNGIE | G8313A | tRNA Lys |
| MT-TK | *MELAS | T8316C | tRNA Lys |
| MT-TK | *Mitochondrial cytopathy | A8326G | tRNA Lys |
| MT-TK | *Mitochondrial Encephalopathy | G8328A | tRNA Lys |
| MT-TK | *PEO and Myoclonus | G8342A | tRNA Lys |
| MT-TK | *MERRF | A8344G | tRNA Lys |
| MT-TK | *Cardiomyopathy | A8348G | tRNA Lys |
| MT-TK | *Myopathy | T8355C | tRNA Lys |
| MT-TK | *MERRF | T8356C | tRNA Lys |
| MT-TK | *MERRF | G8361A | tRNA Lys |
| MT-TK | *Myopathy | T8362G | tRNA Lys |
| MT-TK | *MICM + DEAF/MERRF/Autism | G8363A | tRNA Lys |

-continued

| Locus | Disease | Allele | RNA |
|---|---|---|---|
| MT-TG | *MHCM | T9997C | tRNA Gly |
| MT-TG | *CIPO/Encephalopathy | A10006G | tRNA Gly |
| MT-TG | *PEM | T10010C | tRNA Gly |
| MT-TG | *Myopathy | G10014A | tRNA Gly |
| MT-TG | *GER/SIDS | A10044G | tRNA Gly |
| MT-TH | *MERRF-MELAS/ Cerebral edema | G12147A | tRNA His |
| MT-TH | *RP + DEAF | G12183A | tRNA His |
| MT-TH | *MICM | G12192A | tRNA His |
| MT-TS2 | *CIPO | C12246A | tRNA Ser (AGY) |
| MT-TS2 | *DMDF | C12258A | tRNA Ser (AGY) |
| MT-TL2 | *CPEO | G12294A | tRNA Leu (CUN) |
| MT-TL2 | *Dilated Cardiomyopathy | T12297C | tRNA Leu (CUN) |
| MT-TL2 | *CPEO/Stroke/ CM/Renal & Prostate Cancer Risk | A12308G | tRNA Leu (CUN) |
| MT-TL2 | *CPEO | T12311C | tRNA Leu (CUN) |
| MT-TL2 | *CPEO | G12315A | tRNA Leu (CUN) |
| MT-TL2 | *MM | A12320G | tRNA Leu (CUN) |
| MT-TE | *MM + DM | T14709C | tRNA Glu |
| MT-TT | *Encephalomyopathy | G15915A | tRNA Thr |
| MT-TT | *LIMM | A15923G | tRNA Thr |
| MT-TT | *LIMM | A15924G | tRNA Thr |
| MT-TT | *Multiple Sclerosis | G15927A | tRNA Thr |
| MT-TT | *Multiple Sclerosis | G15928A | tRNA Thr |
| MT-TT | *MM | T15940delT | tRNA Thr |
| MT-TT | *LHON modulator | A15951G | tRNA Thr |
| MT-TP | *MM | C15990T | tRNA Pro |
| MT-TP | *Mitochondrial cytopathy | G15995A | tRNA Pro |

Notes:
LHON: Leber Hereditary Optic Neuropathy; MM: Mitochondrial Myopathy; AD: Alzeimer's Disease; LIMM: Lethal Infantile Mitochondrial Myopathy; ADPD: Alzheimer's Disease and Parkinson's Disease; MMC: Maternal Myopathy and Cardiomyopathy; NARP: Neurogenic muscle weakness, Ataxia, and Retinitis Pigmentosa; alternate phenotype at this locus is reported as Leigh Disease; FICP: Fatal Infantile Cardiomyopathy Plus, a MELAS-associated cardiomyopathy; MELAS: Mitochondrial Encephalomyopathy, Lactic Acidosis, and Stroke-like episodes; LDYT: Leber's hereditary optic neuropathy and DYsTonia; MERRF: Myoclonic Epilepsy and Ragged Red Muscle Fibers; MHCM: Maternally inherited Hypertrophic CardioMyopathy; CPEO: Chronic Progressive External Ophthalmoplegia; KSS: Kearns Sayre Syndrome; DM: Diabetes Mellitus; DMDF: Diabetes Mellitus + DeaFness; CIPO: Chronic Intestinal Pseudoobstruction with myopathy and Ophthalmoplegia; DEAF: Maternally inherited DEAFness or aminoglycoside-induced DEAFness; PEM: Progressive encephalopathy; SNHL: SensoriNeural Hearing Loss Leber Hereditary Optic Neuropathy (LHON) was the first disease for which a mtDNA point mutation was identified. LHON usually presents as a bilateral loss of central vision that typically progresses over weeks without pain, until bilateral scotomas remain. The mean age of onset is in the mid-20's, although the range is extremely broad. Initially, the optic disc may be swollen and the peripapillary retinal nerve fiber layer edematous, then the optic disc atrophies. A common feature during the acute phase of LHON is peripapillary microangiopathy, which was first described by Leber in 1871. Histopathology of end stage nerves shows degeneration and secondary demyelination that likely limits spontaneous recovery of vision in 90% of patients with the G11778A point mutation. The pattern visual evoked potential (VEP) is affected in the early stages of LHON and becomes extinguished at the atrophic stage, indicating the loss of function of retinal ganglion cells. Nevertheless, electroretinograms (ERG) remain normal, suggesting the maintenance of photoreceptor cells, bipolar cells and the retinal pigment epithelium. Though LHON is typically monosymptomatic and does not limit life-span, in early onset cases (2-4 years), other organ systems are involved, and are characterized by muscle weakness, general dystonic rigidity, impaired speech and intelligence and short stature.

Most LHON cases are associated with mutations in one of three mitochondrial genes for subunits of NADH ubiquinone oxidoreductase which is complex I of the mitochondrial respiratory chain. This enzyme contains 7 subunits encoded by mtDNA that are intimately associated with the inner mitochondrial membrane and 35 subunits that are encoded by nuclear DNA and imported into the organelle. The connection between LHON and mtDNA was firmly established in 1988, when Wallace and colleagues reported a homoplasmic nucleotide transition from guanosine to adenosine at position 11778, which results in an arginine to histidine substitution in ND4, a subunit of complex I. Since then, several other mutations in genes for NADH dehydrogenase, cytochrome b, cytochrome oxidase or ATP synthase subunits have been identified that also cause familial LHON. Approximately 50% of LHON patients have the G11778A mutation, 20% have the G3460A mutation, which affects the ND1 gene, and 10% have T14484C in the ND6 gene. These three mutations are considered the primary causes of LHON, and each presents a significant risk of blindness. Nevertheless, LHON shows incomplete penetrance and only about 50% of males and 10% of females in LHON families lose vision. In a minority of cases, lack of penetrance can be attributed to heteroplasmy: loss of vision is rare unless more than 70% of the mtDNA population carries the mutation. Heteroplasmy cannot explain the gender bias. Therefore modifier genes leading to physiological or behavioral differences have been offered as possible explanations for the gender bias.

Table 3 shows examples of symptoms and disorders associated with mitochondrial diseases.

TABLE 3

Problems Associated with Mitochondrial Cytopathies

| Organ System | Possible Problems |
|---|---|
| Brain | Developmental delays, mental retardation, dementia, seizures, neuro-psychiatric disturbances, atypical cerebral palsy, migraines, strokes. |
| Nerves | Weakness (which may be intermittent), neuropathic pain, absent reflexes, gastrointestinal problem (gastroesophogeal reflux, delayed gastric emptying, constipation, pseudo-obstruction), fainting, absent or excessive sweating resulting in temperature regulation problems. |
| Muscles | Weakness, hypotonia, cramping, muscle pain. |
| Kidneys | Proximal renal tubular wasting resulting in loss of protein, magnesium, phosphorous, calcium and other electrolytes. |
| Heart | Cardiac conduction defects (heart blocks), cardiomyopathy. |
| Liver | Hypoglycemia (low blood sugar), liver failure. |
| Eyes | Visual loss and blindness. |
| Ears | Hearing loss and deafness. |
| Pancreas | Diabetes and exocrine pancreatic failure (inability to make digestive enzymes). |
| Systemic | Failure to gain weight, short statue, fatigue, respiratory problems including intermittent air hunger. |

Methods of Isolation of Cells

In an embodiment, the compositions described herein are administered in a pharmaceutical composition to a patient and the mitochondrial genes are expressed in the mitochondria of the patient.

In other preferred embodiment, a mitochondrial gene of interest is introduced into cells first prior to administering to a patient. One method includes culturing cells with the compositions of the invention to allow the gene of interest to be delivered into the mitochondria. In some embodiments, these cells can be a patients cells who is being treated for a mitochondrial related disorder. In such a case, cells from a patient are obtained and cultured ex vivo with the compositions to allow the mitochondrial gene to be expressed in the mitochondria. These cells can then be re-administered to the patient. The cells can be from any source including, blood, tissues, organs, muscles, skin, bone marrow and the like. The cells can be from a haplotype matched donor or a patients autologous cells. One of skill in the art would be familiar with obtaining such cells.

Sources of Stem Cells:

Except where otherwise required, the invention can be practiced using stem cells of any vertebrate species. Included are stem cells from humans; as well as non-human primates, domestic animals, livestock, and other non-human mammals in.

Embryonic Stem Cells:

Embryonic stem cells can be isolated from blastocysts of members of the primate species (Thomson et al., *Proc. Natl. Acad. Sci. USA* 92:7844, 1995). Human embryonic stem (hES) cells can be prepared from human blastocyst cells using the techniques described by Thomson et al. (U.S. Pat. No. 5,843,780; *Science* 282:1145, 1998; *Curr. Top. Dev. Biol.* 38:133 ff., 1998) and Reubinoff et al, *Nature Biotech.* 18:399 (2000)).

Briefly, human blastocysts are obtained from human in vivo preimplantation embryos. Alternatively, in vitro fertilized (IVF) embryos can be used, or one-cell human embryos can be expanded to the blastocyst stage (Bongso et al., *Hum Reprod* 4: 706, 1989). Embryos are cultured to the blastocyst stage in G1.2 and G2.2 medium (Gardner et al., *Fertil. Steril.* 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. USA* 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (.about.200 U/mL; Gibco) or by selection of individual colonies by micropipette. Clump sizes of about 50 to 100 cells are optimal.

Antibodies are particularity useful for the preparation of substantially pure stem cells. By "substantially pure" herein is meant that at least about 50% of the cells present after sorting are stem cells, with at least about 70% preferred and at least about 90% preferred.

Appropriate markers or antigens for detecting bone marrow derived cells (BMDC) are polypeptides or nucleic acids not normally found in tissues outside of the bone marrow. Examples of such markers include, but are not limited to, Flk-1 (Swissprot: locus VGR2_HUMAN, accession P35968), Sca-1 (Swissprot: locus ICE3_HUMAN, accession P42574), Thy-1 (Swissprot: locus THY1_HUMAN, accession P04216), Patched (Accession NP—000255.1 GI:4506247), CXCR (NP—003458.1 GI:4503175), survivin (Swissprot: locus BIR5_HUMAN, accession 015392), and the human homolog of mouse nucleostatin (NP—705775.1 GI:23956324) polypeptides and nucleic acids encoding all or a portion of these proteins. These polypeptides and nucleic acids can be readily obtained using methods well-known to those skilled in the art. Other BMDC markers can also be identified, for example, using transcriptional profiling techniques well-known to those skilled in the art, which can be used to determine the expression of specific subsets of genes in BMDC's and not in non-BMDC tissues. Immunological based diagnostic and prognostic assays such as those described herein, utilize an antibody that is specific for a BMDC polypeptide (i.e., an antigen normally found only in BMDC's) which can be a polyclonal antibody or a monoclonal antibody and in a preferred embodiment is a labeled antibody.

In one preferred embodiment, the population of stem cells is purified. A purified population of stem cells contains a significantly higher proportion of stem cells than the crude population of cells from which the stem cells are isolated. For example, the purification procedure should lead at least to a five fold increase, preferably at least a ten fold increase, more preferably at least a fifteen fold increase, most preferably at least a twenty fold increase, and optimally at least a twenty-five fold increase in stem cells with respect to the total population. The purified population of stem cells should include at least 15%, preferably at least 20%, more preferably at least 25%, most preferably at least 35%, and optimally at least 50% of stem cells.

The purified population of stem cells may be isolated by contacting a crude mixture of cells containing a population of stem cells that express an antigen characteristic of stem cells with a molecule that binds specifically to the extracellular portion of the antigen. Such a technique is known as positive selection.

The amount of cells administered to the patient will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, more preferably, about $1 \times 10^9$ to about $1 \times 10^{10}$ cells are utilized for adult humans. These amounts will vary depending on the age, weight, size, condition, sex of the patient, the type of tumor to be treated, the route of administration, whether the treatment is regional or systemic, and other factors. Those skilled in the art should be readily able to derive appropriate dosages and schedules of administration to suit the specific circumstance and needs of the patient.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated $CD8^+$ cells via intravenous infusion is appropriate.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

DNA Delivery to Mitochondria for Gene Therapy of Diseases

Methods:

To direct the targeting of the AAV vector into the mitochondria we inserted GFP cDNA under the direction of a mitochondrial targeting sequence (MTS) into a modified AAV capsid. We modified this vector by adding the COX8 MTS. It was linked to GFP and inserted into VP2 capsid of AAV at unique EAGI sites. We then linked a normal (wild-type) mitochondrial-encoded ND4 subunit gene with an appended FLAG epitope to a mitochondrial promoter, the H strand promoter in an AAV backbone containing the inverted terminal repeats. This plasmid, pTR-UF11mitoND4, was enveloped by the mitochondrial targeted COX8 MTS-GFP AAV was delivered to human 293 cells and LHON cybrids homoplasmic for the G11778A mutation in mitochondrial DNA. Mitochondria were labeled by MitoTracker Red. To prove the entire AAV virion was directed to mitochondria we co-stained with a conformation antibody (A20) that recognizes only the fully assembled virus. ND4FLAG expression was detected in a one step incubation with anti-FLAG-Cy3 conjugated antibody. We also isolated mtDNA from the transfected homoplasmic LHON cybrids using PCR primers flanking the H strand promoter and the 3' mitoND4. With these primers the endogenous mitochondrial DNA would produce a gene product >10 Kb, while our H strand ND4 AAV should produce a 1.3 Kb product. We selected a PCR extension time of two minutes, too short for amplification of the endogenous mitochondrial DNA.

Results:—

We found the translocation of viral capsid particles expressing GFP to mitochondria, by co-localization with the mitochondrial specific dye MitoTracker. In addition, the A20 specific antibody co-localized with COX8 MTS-GFP suggested import of the fully assembled virion. ND4FLAG expression was detected in the infected cells. Agarose gel electrophoresis of the isolated mtDNA of transfected LHON cybrids revealed the 1.3 Kb band, indicating that our modified AAV vector did indeed deliver the normal ND4 subunit gene to the mitochondria of homoplasmic LHON cybrid cells, thus creating a heteroplasmic allele expressing both wild-type and mutated mtDNA.

Conclusions:—

Our findings suggest that a modified AAV vector may be used to deliver a gene directly to the mitochondria, thus offering hope for the treatment of patients with diseases caused by mutated mitochondrial DNA.

Example 2

Design and Test the Ability of a Modified AAV Vector for Import into Mitochondria Materials and Methods Construction of ND4 and AAV Vectors—

AAV capsid VP2 are modified to accommodate a mitochondrial targeting sequence (COX8, ATPc) and GFP reporter. The AAV backbone pTR-UF11 is used to accept the wild-type ND4 in the mitochondrial genetic code linked to the mitochondrial H strand promoter. The rAAVs are packaged as described by Warrington et al (*J Virol* 2004; 78:6595-6609).

Cell Culture and Transfection—

The study of the pathophysiology of mtDNA mutations has taken advantage of the use of trans-mitochondrial cell lines known as cybrids (King M P, Attardi G. Mitochondria-mediated transformation of human rho$^0$ cells. In Attardi G M, Chomyn A (eds). Mitochondrial Biogenesis and Genetics. San Diego: Academic Press; 1996:313-334). Cybrids are created by fusion of enucleated cells from patients with mutated mtDNA, in this case the G11778A mutation, with cells that have permanently lost their mtDNA after chronic exposure to ethidium bromide (ρ0). This procedure results in the production of a cell line with the mutated mtDNA of the patient and the "neutral" nuclear DNA of the host cell line. Unlike cybrids that contain mutated mtDNA, here the hybrids contain both the normal host cell mutant mtDNA and the AAV delivered wild-type ND4 gene, by using osteosarcoma (143B.TK-) derived human cells containing the wild-type mtDNA. For AAV infections, the appropriate cell line at approximately 50-80% confluency will be transfected with 1 μg of DNA with TransIT Transfection Reagent (Minis) or $3.0 \times 10^{10}$ rAAV viral particles in complete high-glucose medium. Selection in galactose containing media is performed in separate wells, with the cells treated with the selective media for three to five days. Cells infected with the AAV delivered ND4 gene should be somewhat resistant to galactose induced cell death while those mock-infected should be more sensitive and die out. The infected cells and mock-infected controls are trypsinized then quantitated using an automated Coulter Z-100 particle counter present in the PI's lab.

Immunological Techniques & Microscopy—

For immunohistochemistry, the transfected cells are trypsinized and grown on glass slides. After the cells reach confluence they are incubated for 20 min with 250 nM of the mitochondrial-specific fluorescent dye MitoTracker Red or Green (Molecular Probes). Immunostaining of these cells or ocular tissues with mouse monoclonal anti-FLAG M2 antibodies (Sigma Immunochemicals), A20 antibodies or anti-GFP antibodies (Clontech), the latter to increase detection of cells with low levels of GFP expression, is performed. Secondary anti-mouse or anti-rabbit Cy2 (Jackson Immunochemicals) is used for immunodetection Immunofluorescence is visualized on a fluorescent microscope or in a BioRad Confocal Microscope. The collected digital images are pseudocolored red or green for MitoTracker, red for FLAG or green for GFP depending on the experiment then merged in RGB format for evaluation of co-localization. Cells and ocular tissues are further processed for immunogold detection of A20 and ND4FLAG using a Hitachi H7600 TEM. For Western blot analysis, sonicated proteins from mitochondrial lysates obtained from the transfected and restrictive media selected cells and infected ocular tissues are electrophoresed through a 10% polyacrylamide gel and electro-transferred to a polyvinylidene fluoride membrane (Bio-Rad). The membrane is immunostained with mouse monoclonal anti-FLAG M2 or rabbit anti-ND4 antibodies and then with the appropriate HRP-conjugated secondary antibodies and then detected using the ECL system (Amersham).

Oxidative Phosphorylation Assays—

Assays of complex I activity is performed on ND4 and mock-infected cells by the reduction of cytochrome c with NADH and additionally in the presence of the complex I inhibitor rotenone. Values obtained after rotenone inhibition are subtracted from those obtained without rotenone to give complex I activity. ATP synthesis is measured by a modified luciferin-luciferase assay in digitonin permeabilized cells using the complex I substrates malate and pyruvate. ATP synthesis with malate and pyruvate are also measured after the addition of 10 ng/ml oligomycin to completely inhibit mitochondrial ATP production, thus giving us the ATP levels obtained by glycolysis outside the mitochondria. This value is subtracted from the uninhibited ATP levels will give us what we are seeking here, i.e. the value for ATP that is synthesized inside the mitochondrion.

Ribonuclease Protection Assay (RPA)—

To quantify imported ND4 we will measure mRNA levels and endogenous ND4, mitochondrial isolates will be briefly exposed to RNAase to digest any extra-mitochondrial RNA of mock-infected or experimental cells and ocular tissues, at each time point after infection, are prepared by using a RNeasy Mini Kit (Qiagen, Valencia, Calif.) according to the manufacturer's specifications. Each experimental reaction is conducted using an equal amount of RNA. For ND4 analysis, a 297-bp PstI/HindIII fragment of the mouse or a 915-bp SfaNI/SfaNI human ND4 cDNA is sub-cloned into the pT7T3-19 vector and linearized for use as a template in the RPA. The 297-nt or 915-bp antisense probe that is complementary to the target RNA is transcribed with T7 RNA polymerase, (Ambion, Austin, Tex.) in the presence of $\alpha$-$^{32}$P-UTP (ICN, Costa Mesa, Calif.). RPA is carried out using the RPAIII™ kit (Ambion, Austin, Tex.). Gel-purified riboprobes are hybridized with 30 µg mt-RNA at 42° C. for 18 h followed by RNase A/T1 digestion at 37° C. for 30 min Protected fragments are heat denatured and separated on 6% denaturing polyacrylamide gels. A 304 nucleotide mouse β-actin or human antisense probe is used as an internal control. Radioactive signals are recorded and quantitated by using a PhosphorImager. ND4 signal from AAV mediated transfer of the human ND4 gene and the mouse ND4 signal are normalized to the β-actin signal from the same sample, and the normalized values are expressed as a percentage of the signal in the control.

Detection of ROS and Apoptosis—

To detect intracellular ROS generation, two probes are used (Molecular Probes, Eugene, Oreg.). The probe 2'-7' dichlorofluorescein diacetate (DCFDA) is used to detect cytosolic hydrogen peroxide ($H_2O_2$). DCFDA has no fluorescence until it passively diffuses into cells where intracellular esterase cleaves the acetates, and the oxidation of DCFDA by $H_2O_2$ produces a green-fluorescent signal. The mitochondria-specific dye dihydroethidium is used to detect intracellular superoxide. Superoxide oxidizes dihydroethidium to a red fluorescent signal. Cells infected with the AAV expressing mutant ND4 and mock-infected controls are incubated for 15 min at 37° C. with 10 µM of DCFDA & 1 µM of dihydroethidium. We assess apoptotic cell death with a terminal deoxynucleotidyl transferase-mediated dUTP nick end labeling (TUNEL) reaction kit, (Roche, Indianapolis, Ind.) (appendix 3). All labeled cells are washed then observed under a fluorescence microscope and quantitated using a fluorospectrometer.

Morphometric Analysis—

Images of toluidine blue stained sections of the retina and optic nerve are captured with a video camera mounted on a light microscope, and then the data is entered into computer memory. The area of the optic nerve head, intensity of toluidine blue staining and the number of retinal ganglion cells are quantified using the NIH IMAGE software. For statistical analysis, ND4 inoculated eyes are compared with the control eyes that received rAAV-gfp. Statistical analysis is performed by Student's t-test for unpaired data.

Construction of ND4 in the Mitochondrial Genetic Code—

Relative to the lengthy construction of the allotopic allele our next step is to generate an ND4 in the mitochondrial genetic code. The gene is expressed in cells with normal mitochondrial DNA. Therefore, we isolated mitochondrial DNA from human cells with wild-type mtDNA, then used PCR primers designed to amplify the entire ND4 subunit of complex I using a high fidelity polymerase (Pfu). Mutations in this subunit gene are responsible for most cases of LHON. The ND4 derived PCR amplificant will be cloned into the TOPO vector system and colonies screened by direct sequencing.

Construction of a Promoter to Drive Mitochondrial Gene Expression—

To drive mitochondrial gene expression we will first try the heavy (H) strand promoter. Since the mitochondrial H strand promoter is relatively short we annealed the single-stranded oligonucleotide "ggtaccgctgctaacccataccccgaaccaacc-aaac-cccaaagacacccccatctagaa" (SEQ ID NO: 1) to its complementary oligonucleotide "ttctagatgggggtgtctttggggtttggtt-ggttcggggtatgggggttagcagcggtacc" (SEQ ID NO: 2) to comprise a double-stranded H strand gene promoter that we then put into a TOPO vector (Invitrogen) for further cloning. We may incorporate regions of or the entire D loop region to drive ND4 gene expression.

Insertion of the Promoter Gene Construct into pTR-UF Plasmid—

The mitochondrial encoded ND4 subunit gene is linked to the parent AAV pTR-UF11 plasmid from which the hybrid CMV and CBA promoters are removed, and in their place the mitochondrial heavy strand promoter substituted. For the studies of gene expression the ND4 gene is constructed to which the FLAG epitope is appended at the C terminus and the gene for the red fluorescent protein in the mitochondrial genetic code. By using site directed mutagenesis sequences are corrected in the nuclear encoded gene of RFP that are incompatible with the mitochondrial genetic code. This involves changing only three adjacent bases in RFP, thus one mutagenesis. RFP provides a direct way to visualize expression of a gene delivered to mitochondria in living cell culture.

Infection of Cultured Cells with Mito-Targeted VP2 AAV Delivering ND4—

The plasmid pTR-HstrandMitoND4 enveloped by the mitochondrial targeted AAV capsid is delivered to 293 cells, LHON cybrids homoplasmic for the G11778A mutation in mitochondrial DNA (this mtDNA mutation is responsible for most LHON cases) and ρ0 cells. Infected LHON cybrids also expressed GFP that co-localized with MitoTracker Red and silver enhanced A20 immungold. Thus, the AAV virus was targeted to the mitochondria of cells with mutated mitochondrial DNA.

To eliminate the background and further support that wild-type ND4 gene is delivered to the mitochondria ρ0 cells that have absolutely no mitochondrial DNA are infected. We had used this cell line for our previously demonstrated allotopic GFP protein import into mitochondria (Owen R, IV, et al. Recombinant adeno-associated virus vector-based gene transfer for defects in oxidative metabolism. *Hum Gene Ther* 2000; 11:2067-2078). Since these ρ0 cells contain no mitochondrial DNA, any DNA detected in mitochondria isolated from these infected cells would have had to have been delivered by the modified VP2 AAV virus. Controls consist of the VP2 capsid linked to GFP that is not targeted to mitochondria, thus this vector should not deliver the payload ND4 DNA to the mitochondria. Additional controls will consist of using the mito-targeted VP2 to deliver a pTR-UF construct with the CBA promoter driving the allotopic ND4FLAG gene in the universal genetic code.

Anesthesia and Experimental Procedures—

For the intraocular injection of rAAV, 8 week-old DBA/1J mice are sedated by an intramuscular injection of a mixture of ketamine and xylazine. A local anesthetic (proparacaine HCl) is applied topically to the cornea, then a 32-gauge needle attached to a Hamilton syringe is inserted through the pars plana. The needle tip is visualized in the vitreous with the use of the indirect opthalmoscope, and it is positioned directly over the optic nerve head. Two microliters of rAAV-expressing ND4 or RFP are injected into the vitreous of the right eyes of the mice. As controls, the left eyes will receive rAAV with the gfp gene. At the appropriate time after viral inoculations, the mice are sacrificed and the ocular tissues processed for histologic, immunologic, and genes assays.

Magnetic resonance imaging will be performed using a high field 4.7.0 Tesla superconducting magnet (Oxford Instruments Limited) with a SUN computer-based acquisition and processing system (Spectroscopy Imaging Systems) using a 6-cm field of view, a 256×192 matrix with four repetitions and a section thickness of approximately 1.25 mm. A specially designed surface coil is placed over the head for an improved signal-to-noise ratio. Suppression of orbital fat is accomplished using a frequency selective saturation pulse method (1) with a T1 weighting (T1 w)=600 msec and a TE=20 msec. Images are acquired in 3D with the animal lying prone, and sedated as for rAAV injections.

For fMRI non-magnetic light emitting diodes are mounted on the birdcage headcoil directly over the eyes. A flickering at 1 cycle per second is used for visual stimulation protocols. In each experiment, baseline images (no visual stimulation) are acquired for subtraction of the visual signal. Data processing is done by conversion of sequentially sampled data and two-dimensional Fourier transformation. Head movement artifacts are assessed by a center-of-mass analysis. Images are discarded from analysis if the center-of-mass deviation is greater than 25% of a pixel size. For each experiment, the mean image of the prestimulation baseline images is subtracted from the stimulation images on a pixel-by-pixel basis to get a functional map. Usually, 2-4 functional maps are averaged to give a single functional map. Each linearly interpolated map is then overlaid onto the corresponding anatomical image to reveal the location of visual activity in the brain. Since the decussation of the optic nerve at the chiasm is near complete in rodents both eyes are stimulated simultaneously. Therefore, the signal of the experimental right eye is represented in the left brain, and that of the control eye represented in the right brain. Differences in the right and left over regions of interest (ROI) are obtained by subtracting the baseline pre-stimulation values from each of those following stimulation at corresponding time points.

Mean signal intensities over ROIs are used to measure the intensity of T1 weighted and fMRI signals. Regions of interest from the globe to the optic chiasm (T1w MRI) are evaluated. Differences for the right (transduced) and left (control) ROIs of the optic nerves are obtained by subtracting baseline values (obtained prior to intravitreal injections) to the follow-up values obtained after AAV gene inoculations at the corresponding time points. Multivariate analyses of covariance will be used to compare these differences for treatment effect at each follow-up time point. For each analysis, the vector of right and left optic nerve differences is the outcome of interest, baseline values are adjusted for and the effect of treatment is assessed using the Wilks' lambda test. During MRI, all animals are monitored for respiratory rate, pulse and blood oxygen saturation, and body temperature. Respiratory parameters are monitored using a MR compatible respiratory gating circuit consisting of an air-filled balloon lightly attached to the subject's abdomen. Pulse oxymetry will be performed using a footpad IR sensor positioned on the left hindlimb. Body temperature will be monitored using a rectal fluoroptic probe.

Euthanasia.

For evaluations at the end of the in vivo experiments, animals will be sedated as described above and euthanized with an overdose of pentobarbital, I.M. This method is consistent with the recommendations of the Panel on Euthanasia of the American Veterinary Medical Association.

Results and Discussion:

The vector—

Adeno-associated Virus (AAV) possesses a unique profile of biological properties that may make it useful for gene therapy. AAV can provide long-lasting gene expression in almost all ganglion cells of the retina following intravitreal delivery. In contrast, Ad-based vectors can also infect a wide variety of cell types, but their clinical usefulness is limited by their tendency to elicit significant inflammatory and immune responses.

A notable characteristic of AAV is its latency phase, during which it establishes a persistent infection with very little host response. AAV is a single-stranded DNA parvovirus with a 4.7 kb genome and a particle diameter of approximately 20 nm. The AAV genome consists of two genes, rep and cap, which encode the non-structural Rep proteins (Rep78, Rep68, Rep52, and Rep40) and the capsid proteins (VP1, VP2, and VP3), respectively. Flanking these two genes are the inverted terminal repeat (ITR) sequences that provide all the cis-acting sequence required for replication, packaging and integration.

Allotopic Expression—

Using the AAV vector we adapted the approach of allotopic complementation in which a nuclear-encoded version of a gene normally encoded in mitochondrial DNA (ND4 in this case) specifies a protein expressed in the cytoplasm that is then imported into the mitochondria. To accomplish this goal we first constructed a synthetic full-length version of nuclear-encoded ND4 by PCR of overlapping 80 mer oligonucleotides that converted codons read in a non-canonical fashion by the mitochondrial genetic system to the universal genetic code. We appended to this re-coded ND4 gene sequences specifying either the N-terminal region of 1) the P1 isoform of subunit c of human ATP synthase (ATPc) containing the entire 61-amino-acid mitochondrial transport signal (MTS) plus the first 5 amino acids of the mature P1 polypeptide or 2) the aldehyde dehydrogenase (Aldh) containing the first 19 amino-acid MTS. For detection of import we added the short FLAG epitope tag to the C-terminus of the P1ND4 gene or the larger green fluorescent protein (GFP) to the AldhND4 gene.

Even though GFP was successfully imported into mitochondria by an MTS fused to the N-terminus thus making successful transfection easily detectable in living cell culture, when GFP or HA 55 was fused at the C-terminus to a re-coded mitochondrial gene (ND4 or ATP6) import of the fusion protein was unsuccessful. When fused to the FLAG epitope import was successful. To achieve stable and efficient expression of the fusion gene in cells, P1ND4FLAG was inserted into the AAV vectors, pTR-UF11 and pTR-UF12. The chicken β-actin promoter and CMV enhancer drive transgene expression in both vectors. In addition, pTR-UF12 also contains an internal ribosome entry site (IRES) linked to GFP for identification of transfected cells in living cell cultures. Thus, GFP (lacking a MTS) is expressed only in the cytoplasm, while the P1ND4FLAG fusion protein is expressed in the mitochondria of the same cell. Unlike plasmid transfection that requires the addition of chemical reagents to facilitate DNA entry into cells and produces only transient expression of the introduced gene, viral-mediated gene transfer permits efficient delivery of genes into cells and tissues for assays of transgene function.

Transduction of homoplasmic human cybrid cells containing the mitochondria of patients with the G11778A mutation in mtDNA with rAAV containing the P1ND4FLAG fusion gene showed that the ATPc mitochondrial targeting sequence directed the allotopically-expressed ND4FLAG polypeptide into mitochondria. Cells transfected with P1ND4FLAG in AAV vector pTR-UF11 showed mitochondrially targeted FLAG that co-localized with MitoTracker Red. Cells transfected with a COX8 MTS directing GFP import into mitochondria do show co-localization of GFP and MitoTracker Red. Lastly, when ND4 was linked to GFP rather than FLAG the ND4GFP fusion did have a punctate staining pattern suggestive of import into mitochondria, but the poor co-localization of GFP with MitoTracker Red indicates that this fusion did not efficiently import or assemble in the mitochondrial matrix. The 52 Kd size of the imported ND4FLAG on SDS polyacrylamide gels was consistent with that of the imported fusion polypeptide.

AAV as a Vehicle for Import of DNA into Mitochondria—

Next, we asked if this technique could be modified to direct import of AAV to deliver a DNA payload, in this case the ND4 subunit gene, directly into the mitochondria. This technique differs from allotopic expression in which a mitochondrial gene was recoded in the nuclear genetic code and the translated protein then directed from the cytoplasm to mitochondria by a targeting sequence. Rather, here we would attempt to target the AAV to deliver its DNA payload directly to the mitochondrion for expression in the organelle. The VP2 capsid protein of AAV-2, the serotype best known for infection of retinal ganglion cells, can tolerate large peptide insertions at the N terminus. Remarkably, this insertion did not substantially reduce infectivity of the recombinant AAV. Direct insertion of amino acid sequences into the AAV-2 capsid open reading frame (cap ORF) is one strategy to redirect the targeting of the prototypical gene therapy vector. Using this system nearly wild-type levels of recombinant AAV-like particles were obtained even with ligands as large as 30-kDa inserted into VP2. Insertions at residue 138 in VP2 had a minimal effect on viral infectivity.

To direct the targeting of the AAV vector into the mitochondria we inserted GFP under the direction of a mitochondrial targeting sequence (MTS) into the modified AAV capsid provided to us by the Muzyczka laboratory. We modified this vector by adding the COX8 MTS that we had used above for allotopic expression of GFP into mitochondria. Here it was linked to GFP (purple) and inserted into the VP2 capsid at unique EAGI sites at residue 138.

It was our expectation that this vector should generate an AAV virion whose trafficking within the cell and import into the mitochondria can be monitored in cultured cells by fluorescence microscopy, as we had previously demonstrated for the allotopic expression of GFP. Unlike allotopic complementation that delivers the gene to the nucleus (with the expressed protein imported from the cytoplasm into the mitochondria) here we are attempting to deliver the DNA encoding the ND4 gene directly into the mitochondria.

To test our hypothesis we infected human 293 cells with the COX8MTS-GFP AAV particles. Indeed, we found the translocation of viral capsid particles expressing GFP to mitochondria, by co-localization with the mitochondrial specific dye MitoTracker Red.

To show that the entire AAV virion was directed to mitochondria we co-stained with a conformation antibody (A20) that recognizes only the fully assembled viruses. We found the silver enhanced immunogold stained conformational A20 specific antibody co-localized with COX8MTS-GFP. Thus, this finding indicates that the viruses are indeed targeted to the mitochondria.

Testing the Ability of the Modified AAV Virion to Deliver the Payload DNA to the Target Mitochondrion.

To achieve this next step we isolated mitochondrial DNA from human cells with wild-type mtDNA, then used PCR primers designed to amplify the entire ND4 subunit of complex I. Mutations in this subunit gene are responsible for most cases of LHON. The ND4 gene that we had designed for allotopic expression in our previous work was in the nuclear genetic code, thus not suitable for expression in mitochondria. However, it could provide an important control experiment, i.e. when delivered by our modified AAV it should not direct synthesis within mitochondria but only in the cytoplasm. If it did then this finding would suggest that the modified AAV delivered the ND4 payload to the nucleus rather than to the mitochondria.

Errors in the amplified ND4 gene in the mitochondrial genetic code were corrected by site directed mutagenesis. We then linked this mitochondrial encoded ND4 subunit gene to a mitochondrial promoter, the heavy H strand promoter in an AVV backbone (pTR-UF) containing the inverted terminal repeats (iTRs). This plasmid pTR-UF11mitoND4 enveloped by the mitochondrial targeted AAV capsid was delivered to cells homoplasmic for the G11778A mutation in mitochondrial DNA. This mtDNA mutation is responsible for most LHON cases. As was the case for the human 293 cells these LHON cybrids also expressed COX8GFP that co-localized with MitoTracker Red and silver enhanced A20 immunogold. Thus, the AAV virion was targeted to the mitochondria of cells with mutated mitochondrial DNA.

Next, we selected infected cells expressing the wild-type ND4 gene product using glucose-free galactose media, as we had done for the allotopic expression of ND4 and ATP with the FLAG epitope. After 5 days of selection in glucose-free galactose media, the cells were amplified for several weeks in normal media then the mitochondria were isolated. The mtDNA was then isolated from this mito pellet. To test, whether the mito-pellet contained the wild-type ND4 gene delivered by our modified mito-targeted AAV vectors, we designed PCR primers with the forward one flanking the H strand promoter and the reverse one flanking the mitoND4. Using these primers the endogenous mitochondrial DNA would produce a gene product >10 Kb while our H strand ND4 AAV should produce a 1.3 Kb product. To detect our AAV gene product we selected a PCR extension time of two minutes, too short for amplification of the endogenous mitochondrial DNA.

We found the presence of the 1.3 KB band, indicating that our modified AAV vector did indeed deliver its payload DNA (the mitochondrially encoded ND4 subunit gene) to the mitochondria. To further test this hypothesis we performed an SfaNI digest. There are two SfaNI sites in the wild-type ND4 gene. The G11778A mutation in mtDNA results in loss of one of these, thus only one is present in the LHON mutated mitochondrial ND4 subunit gene. With two sites the largest digestion product should be 915 base pairs, but 1.2 Kb with only the one site present in mutated LHON mtDNA. The SfaNI digest revealed a 915 bp band indicating the presence of two SfaNI sites, thus characteristic of the wild-type mitochondrial ND4 DNA inserted by our modified AAV vector. This finding was confined by loss of the Mae III restriction site induced by the G to A transition at nucleotide 11778 in the mutated ND4 LHON DNA of the cybrids.

Next, we measured the degree of heteroplasmy introduced by the mito-targeted AAV ND4 subunit DNA into LHON cybrid cells harboring 100% mutated mtDNA with the A transition at nucleotide 11778. For this experiment we used PCR primers designed to amplify only the ND4 gene encompassing the 11778 nucleotide region, between the forward and reverse primers. On the sequencing chromatograph the G peak at nucleotide position 11778 measured 94 and the A peak measured 503. Therefore, the degree of heteroplasmy introduced by the mito-targeted AAV was 19%, small but large enough to get a measurable effect. Growth of the LHON cybrid cells in the glucose-free galactose media after five days suggests that the LHON cells received, expressed and were rescued by the wild-type ND4 subunit unit gene that we delivered with the mitochondrially targeted AAV. These same cells infected with the standard AAV-2 lacking the mitochondrial targeting sequence in the VP2 capsid all died after five days in the glucose-free galactose media.

Test the Ability of the Mitochondrion to Express the AAV Delivered DNA:

To demonstrate expression of the mitochondrial gene product we will use the modified COX8MTSGFP AAV VP2 capsid to deliver to the mitochondria the pTR-UF plasmid containing the mitochondrial heavy (H) strand promoter driving expression of a red fluorescent protein (RFP) in the mitochondrial genetic code that we are already constructing by using site directed mutagenesis of the nuclear version of RFP. Bennett and co-workers used a similar version of RFP in the mitochondrial genetic code, driven by the H strand promoter to demonstrate mitochondrial gene expression (Khan S M, et al. *J Bioenerg Biomembr* 2004; 36:387-393). In addition, we are adding to the ND4 subunit gene described above the FLAG epitope appended to the C terminus, all in the mitochondrial genetic code. We will then detect RFP and the ND4FLAG fusion proteins in mitochondria by fluorescence co-localization with MitoTracker green, and the ND4FLAG fusion protein by immunogold and transmission electron microscopy. We have successfully demonstrated allotopic expression of the FLAG epitope fused in frame to the nuclear encoded version of the ND4 and ATP6 subunit genes. We have also successfully demonstrated allotopic expression of GFP. Since the publication of those results we have used electron microscopy to demonstrate the expression of the ND4FLAG fusion protein in mitochondria both in cell culture and in the mouse optic nerve. In transmission electron micrographs we show immunogold labeled FLAG is present in mitochondria of human 293 cells.

The Ability of the Mitochondrially Targeted AAV Containing a Normal ND4 Gene to Rescue the Defective Respiration of LHON Cells with Mutated mtDNA:

To determine if import led to functional complementation with the wild-type ND4, homoplasmic cybrid cells harboring mutant mtDNA (i.e. 100% G11778A mtDNA derived from a patient with LHON inserted into a neutral nuclear background) were infected with our modified AAV with the mitochondrial targeted VP2 capsid enveloping the pTR-UF plasmid containing the wild-type ND4 subunit gene, then tested for rescue by measuring cell growth in glucose-deficient galactose media. Cells harboring complex I mutations have a severe growth defect compared to wild-type cells in such medium. After 48 hours of growth in galactose we found a 19% increase in cell survival ($p<0.05$) relative to controls, the cybrid cells infected with the same ND4 gene but in a virus without the MTS attached to the GFP expressing VP2. We have found that increasing the DNA concentration 3 fold results in some colonies of cybrid cells infected with the mitochondrial targeted VP2 surviving after 5 days in galactose, while the controls infected with the VP2 capsid that did not contain the MTS all died. One plausible explanation is that the galactose medium selected for infected cybrids expressed wild-type ND4, suggesting these cells likely had improved respiration.

Since assays of complex I activity revealed no significant differences between G11778A mutant cybrids and the wild-type cell line, we were unable to measure a difference in NADH-dehydrogenase activity as a result of transduction with allotopically expressed ND4FLAG. Therefore, we here focused on changes in ATP synthesis using the complex I substrates malate and pyruvate as substrates for oxidative phosphorylation. Relative to the wild-type cell line with normal mtDNA, untreated cybrid cells with the G11778A mtDNA have a 60% reduction in the level of ATP synthesis. Allotopic expression of a normal ND4 reversed this deficiency in ATP synthesis. Relative to control G11778A cybrids transfected with a AAV-GFP, G11778A cybrids infected with P1ND4F showed a 3-fold increase in the rate of ATP synthesis, thus leading to ATP production that was statistically indistinguishable from the corresponding wild-type cell-line. Therefore, we expect that if our new approach to append the COX8 mitochondrial targeting sequence driving GFP expression in the AAV VP2 capsid results in the translocation of AAV containing the pTR-UF plasmid expressing the wild-type ND4 gene into the mitochondria of respiratory deficient LHON cells then ATP synthesis should improve. We found a 48% increase in the rate of ATP synthesis in LHON cybrids infected with the mito-targeted AAV expressing wild-type ND4 relative to control LHON cells infected with the AAV vector lacking the MTS. This difference was statistically significant ($p<0.05$) ($n=7$). Thus, we improved mitochondrial respiration by the ND4 gene transfer.

Expression of AAV Delivered DNA by Mitochondria:

Mitochondrially targeted VP2 capsid AAV is used to deliver the mitochondrial H strand promoter to drive expression of a mitochondrial encoded red fluorescent protein (RFP) or ND4 subunit gene to which the FLAG epitope is appended to the C terminus and inserted into the pTR-UF backbone. Expression of RFP and the ND4FLAG fusion is detected in mitochondria by fluorescence co-localization with MitoTracker and confirmation of FLAG immunogold within mitochondria by transmission electron microscopy.

Detection of Expression of AAV Transferred ND4 & RFP—

Human 293 cells containing normal mtDNA, LHON cybrids with 100% mutated mitochondrial DNA (G1177A) and ρ0 cells without mitochondrial DNA are infected with the mitochondrially targeted AAV VP2 containing the MTS, but without the GFP reporter and containing the payload ND4FLAG fusion gene or RFP in the mitochondrial genetic code. They are then be tested for expression of the fusion polypeptide. To determine if the mitochondrially targeted VP2 capsid AAV directed the expression of ND4FLAG or RFP in mitochondria, immunocytochemistry is used to detect the FLAG epitope in the infected cells and direct visualization of red fluorescent protein by fluorescence microscopy. Mitochondrial expression of RFP and immunostaining with anti-FLAG antibody linked to cy2 (red) should reveal a typical punctate mitochondrial pattern each co-localizing with the mitochondrion-specific dye (in this case MitoTracker Green). That these reporters were expressed in mitochondria fluorescence microscopy, is confirmed by the detection of FLAG tagged immunogold within mitochondria by using transmission electron microscopy. Additionally, detection of FLAG in mitochondrial isolates from these infected cells by immunoblotting is taken as evidence that the fusion protein containing the wild-type ND4 linked to FLAG was expressed.

Mitochondrially Targeted AAV Containing a Normal ND4 Gene Rescue of the Defective Respiration of LHON Cells with Mutated mtDNA:

Cells homoplasmic for the G11778A mutation in mtDNA in a neutral nuclear background will be infected and then tested for rescue by measuring cell growth (in glucose-deficient galactose media), apoptosis, cellular respiration and ROS production.

While the study of the pathophysiology of mtDNA mutations has taken advantage of the use of transmitochondrial hybrid cell lines known as cybrids, we are now in a position to study the effects of a hetero-allelic hybrid cell line expressing both mutant ND4 and the wild-type ND4 delivered by AAV. Using our hybrids we will gauge the effects of the normal ND4 allele on cellular function relative to the homoplasmic cybrids with 100% mutated ND4 mtDNA by assays of cell growth, apoptosis, oxidative phosphorylation and ROS production.

Cell Survival Following ND4 Gene Transfer—

To determine protective effect, cells homoplasmic for the G11778A LHON mutation in mitochondrial DNA are infected. To determine the impact of the transferred ND4 DNA, the growth of transfected cells are evaluated in selective media that forces the cells to rely on the respiratory chain to produce ATP Immediately following the infection with AAV-expressing ND4, cells with 100% mutated LHON mtDNA are grown in the standard glucose-rich medium for 3 days. They are placed in glucose-free medium containing galactose as the main carbon source for glycolysis. This medium forces the cells to rely predominantly on oxidative phosphorylation to produce ATP. Cells harboring complex I mutations have a severe growth defect compared to wild-type cells in such media. The number of cells relative to mock-infected cells placed in this selective media are counted. This latter approach should select for cells expressing the highest levels of wild-type ND4, for testing of its impact on oxidative phosphorylation and ROS production later. The colonies of ND4 transfected LHON cells will not die out, thus cell counts should be greater in these culture plates relative to mock infected cultures. This finding will be confirmed by immunostaining of the surviving cells for the FLAG epitope.

Oxidative Phosphorylation Rescue by ND4—

Assays of complex I activity by spectrophotometric measurements of the NADH reduction of cytochrome c in cells expressing the AAV delivered ND4FLAG relative to mock-infected cells are performed. To obtain the mitochondrial complex I activity, the value obtained after the addition of the complex I inhibitor rotenone are subtracted from the initial total value and expressed relative to the protein content of the sample.

Complexes I to V of the respiratory chain result in the generation of ATP. As a measure of oxidative phosphorylation, we will focus on increases in ATP synthesis induced by the AAV mediated gene transfer by using malate and pyruvate as complex I substrates. We have already shown that relative to the wild-type cell line with normal mtDNA, cybrid cells containing the LHON G11778A mutation in mtDNA had a 60% reduction in the rate of ATP synthesis. Such substantial reductions in ATP synthesis likely contribute to the development of optic neuropathy in LHON patients with the G11778A mtDNA mutation.

We found that allotopic expression of a normal ND4 reversed this deficiency in ATP synthesis. Relative to control G11778A cybrids infected with a AAV-GFP, G11778A cybrids infected with the allotopic P1ND4FLAG showed a 3-fold increase in the rate of ATP synthesis, thus leading to ATP production that was statistically indistinguishable from the corresponding wild-type cell-line. We expect that if appending the COX8 mitochondrial targeting in the AAV VP2 capsid results in the translocation of AAV containing the pTR-UF plasmid expressing the wild type ND4 gene into the mitochondria of respiratory deficient LHON, then ATP synthesis should improve. LHON cybrids are infected with the MTS modified VP2 AAV containing the ND4 gene expressed in the mitochondrial genetic code, then measure ATP synthesis.

To measure the kinetics of ATP synthesis in cells the chemiluminescence generated by endogenous cellular ATP in the presence of a luciferin-luciferase cocktail is used. This assay was modified by permeablizing the cells with digitonin as the last step before measuring chemiluminescence. This modification prevents loss of cellular ATP prior to measurements, thus resulting in more accurate measures of cellular ATP that were higher than had been previously reported with the two-minute digitonin treatment and centrifugation, which resulted in loss of cellular ATP after washing out the digitonin and resuspending the cells in buffer.

Since cell lines infected with the wild-type ND4 will still harbor high levels of mutant ND4 mtDNA, the levels of increases in ATP synthesis are not predicted to be as significant as seen in the parental osteosarcoma cells with 100% wild-type ND4. However, we do expect the levels of increases in ATP synthesis in our hybrids to reflect the ratio of the allotopically expressed wild-type ND4 and the mutant R340H ND4 indigenous to the cell line.

We have shown the rate of ATP synthesis increased by 48% in LHON cybrids infected with the mito-targeted AAV expressing wild-type ND4 relative to control LHON cells infected with the AAV vector lacking the MTS. This difference was statistically significant ($p<0.05$) ($n=7$). Thus, mitochondrial respiration was improved by the ND4 gene transfer using the COX8 mitochondrial targeting sequence-GFP appended to the VP2 capsid of AAV. We expect that higher levels of ATP synthesis may be achieved by delivering higher levels of wild-type ND4 DNA than shown in our preliminary results. This may be achieved by using alternative (ATPc) or tandem targeting sequence appended to VP2 and by deleting the GFP reporter.

In support of oxidative phosphorylation deficiency as a mechanism for optic neuropathy, we have demonstrated that attacking expression of a critical complex I subunit gene (NDUFA1) reduces complex I activity by 80% and induces degeneration of the optic nerve in the mouse, with features similar to human LHON also caused by defective complex I subunit genes. Still reactive oxygen species also play a role, as we were able to rescue the optic neuropathy induced by complex I deficiency using an anti-ROS gene (SOD2) coding for the mitochondrial superoxide dismutase.

Reactive Oxygen Species & Apoptosis Reduced by ND4—

It appears that an inverse relationship exists between the activity of complex I and ROS. In fact, the cytotoxicity induced by loss of complex I activity may not be entirely from reductions in oxidative phosphorylation, but may be due in part to increased production of ROS. Within the mitochondria, production of ROS occurs at complex I and complex III (ubiquinone-cytochrome c oxidoreductase), with complex I being the major source. In LHON, electrons that normally pass along the electron transport chain from complex I to ubiquinone react with molecular oxygen, generating superoxide, thus creating oxidative stress that may in turn damage proteins, lipids, and DNA. This ultimately culminates in cell death and optic neuropathy.

In support of oxygen toxicity as a mechanism for optic neuropathy we have demonstrated that increasing ROS levels directly, by attacking synthesis of an anti-ROS gene (SOD2) that dismutes superoxide, induces optic nerve injury with features similar to LHON caused by mutated complex I subunit genes. Since complex I activity is only mildly reduced in the most common mutation associated with LHON (G11778A), many years may pass before elevated levels of ROS induce an injury to the optic nerve severe enough to result in loss of vision. This may contribute to the delay in the onset of optic neuropathy of LHON patients. However, in cells we are able to obtain the answer more quickly.

To test whether the wild-type ND4 gene transfer to LHON cells infected with rAAV will decrease the generation of reactive oxygen species that induce apoptosis, levels of superoxide and hydrogen peroxide suppression generated by infection with the ND4 gene will be measured, using commercially available kits from Molecular Probes. Relative to mock-infected cells, it is likely that we will find that expression of the wild-type ND4 gene in LHON cybrids decreases the production of ROS. We would expect that gene transfer of the wild-type ND4 will suppress ROS production and apoptosis. Apoptosis is determined using a terminal deoxynucleotidyl transferase-mediated dUTP nick end labeling (TUNEL) reaction kit, (Roche). After the TUNEL reaction, the samples are observed under a fluorescence microscope.

What is claimed:

1. A composition comprising virions, each virion comprising: i) a recombinant viral vector comprising a human mitochondrial gene operably linked to a mitochondrial promoter, and ii) a recombinant viral capsid comprising a mitochondrial targeting sequence,
   wherein the virions are capable of entering mitochondria resulting in expression of the human mitochondrial gene in the mitochondria.

2. The composition of claim 1, wherein the viral vector is a DNA viral vector or an RNA viral vector.

3. The composition of claim 1, wherein the viral vector is selected from the group consisting of: adeno-associated virus (AAV), retrovirus, adenovirus, and alphavirus.

4. The composition of claim 1, wherein the human mitochondrial gene is a wild-type mitochondrial gene and expression thereof in at least one cell compensates for a homologous mitochondrial gene having at least one mutation in the at least one cell.

5. The composition of claim 1, wherein the virions are AAV virions, the recombinant viral vector is a recombinant AAV vector, and the recombinant viral capsid is a recombinant AAV capsid comprising a mitochondrial targeting sequence.

6. The composition of claim 5, wherein the human mitochondrial gene and mitochondrial promoter are interposed between at least one AAV inverted terminal repeat sequence and a second AAV inverted terminal repeat sequence.

7. The composition of claim 5, wherein the recombinant AAV vector is a self-complementary AAV vector.

8. A method of introducing nucleic acid molecules into mitochondria comprising:
   providing a composition comprising virions, each virion comprising: i) a recombinant viral vector comprising a human mitochondrial gene operably linked to a mitochondrial promoter, and ii) a recombinant viral capsid comprising a mitochondrial targeting sequence; and
   introducing the composition into cells having mitochondria, wherein the virions enter the mitochondria and the human mitochondrial gene is expressed in the mitochondria.

9. The method of claim 8, wherein the mitochondrial gene is expressed in the mitochondria and said gene is a wild-type gene which compensates for a mutation associated with a mitochondrial related disease.

10. The method of claim 9, wherein the mitochondrial gene compensates for the mutation in a mitochondrial gene associated with a disease selected from the group consisting of: Alpers Disease; Barth syndrome; .beta.-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Opthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Opthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young, and MNGIE.

11. The method of claim 8, wherein the mitochondrial targeting sequence is selected from the group consisting of: cytochrome c oxidase (COX); ATP synthase; subunit c of human ATP synthase (ATPc); ATP synthase; hexokinase I, amine oxidase (flavin-containing) A, hexokinase IV, pancreatic beta cell form, peripheral benzodiazepine receptor-related protein, metaxin 2, putative mitochondrial outer membrane protein import receptor (hTOM), glutathione transferase; voltage-dependent anion channel 2 (outer mitochondrial membrane protein porin), hexokinase IV, cytochrome b5, peripheral benzodiazepine receptor, germ cell kinase anchor S-AKAP84, A kinase anchor protein, carnitine O-palmitoyltransferase I precursor, hexokinase II, amine oxidase (flavin-containing) B, long-chain-fatty-acid—CoA ligase 2, long-chain-fatty-acid—CoA ligase 1 (palmitoyl-CoA ligase), voltage-dependent anion channel 1, metaxin 1, Human putative outer mitochondrial membrane 34 kDa translocase hTOM34, voltage-dependent anion channel 4 (outer mitochondrial membrane protein porin), cytochrome-b5 reductase, voltage-dependent anion channel 3 (outer mitochondrial membrane protein porin), Mitochondrial import receptor subunit TOM20 homolog (Mitochondrial 20 kd outer membrane protein) (Outer mitochondrial membrane receptor TOM20), and tumorous imaginal discs homolog precursor (HTID-1).

12. The method of claim 8, wherein the cells are in an ex vivo culture; and the cells are administered to a mammalian subject.

13. The method of claim 12, wherein the cells are obtained from organs, skin, tissues, muscles or bone marrow.

14. The method of claim 13, wherein the cells are stem cells.

15. The method of claim 14, wherein the stem cells are autologous; HLA-compatible or partially HLA matched.

16. The method of claim 8, wherein the virions are AAV virions, the recombinant viral vector is a recombinant AAV vector, and the recombinant viral capsid is a recombinant AAV capsid comprising a mitochondrial targeting sequence.

17. The method of claim 16, wherein the recombinant AAV vector is a self-complementary AAV vector.

18. The method of claim 8, wherein the human mitochondrial gene and mitochondrial promoter are interposed between at least one AAV inverted terminal repeat sequence and a second AAV inverted terminal repeat sequence.

* * * * *

UNITED STATES PATENT AND TRADEMARK OFFICE
CERTIFICATE OF CORRECTION

| | | |
|---|---|---|
| PATENT NO. | : 8,278,428 B2 | Page 1 of 1 |
| APPLICATION NO. | : 12/526878 | |
| DATED | : October 2, 2012 | |
| INVENTOR(S) | : John Guy | |

It is certified that error appears in the above-identified patent and that said Letters Patent is hereby corrected as shown below:

In the Specifications:

In column 1, immediately before the "FIELD OF THE INVENTION" section, please insert:

-- STATEMENT AS TO FEDERALLY SPONSORED RESEARCH AND DEVELOPMENT

This invention was made with Government support under Grant No. 1RO1EY017141-01A2, awarded by the National Eye Institute. The Government has certain rights in the invention. --

Signed and Sealed this
Sixteenth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,278,428 B2                                           Page 1 of 1
APPLICATION NO.    : 12/526878
DATED              : October 2, 2012
INVENTOR(S)        : John Guy It is certified that error appears in the above-identified patent and that said Letters Patent is hereby corrected as shown below:

In the Specifications:

In column 1, immediately before the "FIELD OF THE INVENTION" section, please insert:

-- STATEMENT AS TO FEDERALLY SPONSORED RESEARCH AND DEVELOPMENT

This invention was made with Government support under Grant No. 1RO1EY017141-01A2 from the National Institutes of Health, awarded by the National Eye Institute. The Government has certain rights in the invention. --

This certificate supersedes the Certificate of Correction issued July 16, 2013.

Signed and Sealed this
Eighth Day of October, 2013

Teresa Stanek Rea
*Deputy Director of the United States Patent and Trademark Office*